US008703916B2

(12) United States Patent
Chen

(10) Patent No.: US 8,703,916 B2
(45) Date of Patent: *Apr. 22, 2014

(54) B7-H3 AND B7-H4, NOVEL IMMUNOREGULATORY MOLECULES

(75) Inventor: Lieping Chen, Hamden, CT (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/552,247

(22) Filed: Jul. 18, 2012

(65) Prior Publication Data
US 2013/0267685 A1 Oct. 10, 2013

Related U.S. Application Data

(60) Continuation of application No. 13/323,360, filed on Dec. 12, 2011, now Pat. No. 8,236,767, which is a division of application No. 11/929,481, filed on Oct. 30, 2007, now Pat. No. 8,129,347, which is a continuation of application No. 11/120,927, filed on May 2, 2005, now Pat. No. 7,622,565, which is a continuation of application No. 09/915,789, filed on Jul. 26, 2001, now Pat. No. 6,891,030.

(60) Provisional application No. 60/220,991, filed on Jul. 27, 2000.

(51) Int. Cl.
C07K 14/00 (2006.01)

(52) U.S. Cl.
USPC ......................................... 530/350

(58) Field of Classification Search
None
See application file for complete search history.

(56) References Cited

U.S. PATENT DOCUMENTS

| 6,468,546 B1 | 10/2002 | Mitcham et al. ............ 424/277.1 |
| 6,891,030 B2 | 5/2005 | Chen ............................. 536/23.5 |
| 7,189,563 B2 | 3/2007 | Eaton et al. ............... C12N 1/19 |
| 7,304,149 B2 | 12/2007 | Murphy et al. |
| 7,875,702 B2 * | 1/2011 | Chen ............................... 530/350 |
| 8,129,347 B2 | 3/2012 | Chen .............................. 514/21.2 |
| 2002/0165347 A1 | 11/2002 | Fox et al. |
| 2004/0152105 A1 | 8/2004 | Vogt et al. |
| 2004/0175380 A1 | 9/2004 | Allison et al. |
| 2004/0180047 A1 | 9/2004 | Chen et al. |
| 2005/0163772 A1 | 7/2005 | Dong et al. |
| 2008/0160036 A1 | 7/2008 | Chen |
| 2008/0206235 A1 | 8/2008 | Chen |
| 2009/0011444 A1 | 1/2009 | Chen |
| 2009/0142342 A1 | 6/2009 | Chen |
| 2011/0171207 A1 * | 7/2011 | Chen ........................... 424/130.1 |

FOREIGN PATENT DOCUMENTS

| WO | WO99/63088 | 12/1999 |
| WO | WO00/12758 | 3/2000 |
| WO | WO00/36107 | 6/2000 |
| WO | WO02/02587 | 1/2002 |
| WO | WO2011/026122 | 3/2011 |
| WO | WO2011/026132 | 3/2011 |

OTHER PUBLICATIONS

Abbas et al., Cellular and Molecular Immunology, 2nd Ed., pp. 386, 407 and 408 (1994).
Chapoval, et al., B7-H3: a costimulatory molecule for T cell activation and IFN-gamma production, Nat. Immunol., 2(3):269-74 (2001).
Chapoval, et al., "Immunoglobulin fusion proteins as a tool for evaluation of T-cell costimulatory molecules", Methods Mol. Med., 45:247-255 (2000).
Chapoval, et al., "Immunoglobulin fusion proteins as a tool for evaluation of T-cell costimulatory molecules", Mol. Biotechnol., 21:259-64 (2002).
Chen, "Co-inhibitory molecules of the B7-DC28 family in the control of T-cell Immunity", Nat. Rev. Immunol., 4(5):33647 (2004).
Choi, et al., "Genomic organization and expression analysis of B-7H4, an immune inhibitory molecule of the B7 family", J. Immunol., 171:4650-4654 (2003).
Coyle, et al., "The CD28-related molecule ICOS is required for effective T-cell-dependent immune responses", Immunity, 13(1):95-105 (2000).
Coyle, et al., "The expanding B7-superfamily: increasing complexity in costimulatory signals regulating T cell function", Nat. Immunol, 2(3):203-209 (2001).
Coyle et al., Nature Immunol., 2.203-209, 2001.
Faas, et al., "Primary structure and functional characterization of a soluble, alternatively spliced form of B7-1", J. Immunol., 164(12):6340-8 (2000).
Genbank Accession No. AY280972.1 "*Homo sapiens* immune costimulatory protein B7-H4 mRNA, complete cds", 2 pages, submitted Apr. 22, 2003, first published Jun. 1, 2003, accessed Feb. 18, 2009.
Genbank Accession No. AY280972, (2003).
Jeannin, et al., "Soluble CD86 is a costimulatory molecule for human T lymphocytes", Immunity, 13(3):303-312 (2000).
Keir and Sharpe, "The B7/CD28 costimulatory family in autoimmunity", Immunol. Rev., 204:128-143 (2005).
Kinoshita et al., "Costimulation by B7-1 and B7-2 is required for autoimmune disease in MRL-Faslpr mice", J. Immunol, 164(11):6046-6056 (2000).
Krambeck, et al., "B7-H4 expression in renal cell carcinoma and tumor vasculature: associations with cancer progession and survival", Proc. Natl. Acad. Sci. USA, 103(27):10391-10396 (2006).
Kryczek, et al., "B7-H4 expression identifies a novel suppressive macrophage population in human ovarian carcinoma", J. Exp. Med., 203:871-881 (2006).

(Continued)

*Primary Examiner* — Ilia Ouspenski
(74) *Attorney, Agent, or Firm* — Fish & Richardson P.C.

(57) ABSTRACT

The invention provides novel B7-H3 and B7-H4 polypeptides useful for co-stimulating T cells, isolated nucleic acid molecules encoding them, vectors containing the nucleic acid molecules, and cells containing the vectors. Also included are methods of making and using these co-stimulatory polypeptides.

11 Claims, 10 Drawing Sheets

(56) References Cited

OTHER PUBLICATIONS

Kryczek, et al., "Cutting edge: Induction of B7-H4 on APCs through IL-10: novel suppressive mode for regulatory T cells", J. Immunol, 177(1):40-44 (2006).

Li, et al., "Biochemical analysis of the regulatory T cell protein lymphocyte activation gene-3 (LAG-3; CD223)", J Immunol, 172(11):6806-6812 (2004).

Liang, et al., "Autoantibody responses and pathology regulated by B7-1 and B7-2 costimulation in MRL/lpr lupus", J Immunol., 165(6):3436-3443 (2000).

Metzler et al., Nature Structural Biol., 4:527-531, 1997.

Ou, et al., "B7-H4.Ig inhibits human beta-cell destruction mediated by beta cell-specific cytotoxic T cells derived from patients with type 1 diabetes", 54 (Suppl. 1):A311 (2005).

Peasad, et al., "B7S1, a novel B7 family member that negatively regulates T cell activation", Immunity, 18(6):863-873 (2003).

Salceda, et al., "The immunomodulatory protein B7-H4 is overexpressed in breast and ovarian cancers and promotes epithelial cell transformation", Exp. Cell Res., 306(1):128-141 (2005).

Skolnick et al., Trends in biotech., 18(1):34-39, 2000.

Sica, et al., "B7-H4, a molecule of the B7 family, negatively regulates T cell immunity", Immunity, 18:849-861 (2003).

Simon, et al., "B7-H4 is a novel membrane-bound protein and a candidate serum and tissue biomarker for ovarian cancer", Cancer Res., 66(3):1570-1575 (2006).

Suh, et al., "Generation and characterization of B7-H4/B7S1/B7x-deficient mice", Mol. Cell Biol.., 26(17):6403-6411 (2006).

Sun, et al., B7-H3 and B7-H4 expression in non-small-cell lung cancer, Lung Cancer, 53 (2):143-151 (2005).

Sun, et al., "Costimulatory molecule-targeted antibody therapy of a spontaneous autoimmune disease", Nat. Med. 8(12):1405-1413 (2002).

Tamura, et al., "B7-H1 costimulation preferentially enhances CD28-independent T-helper cell function", Blood, 97:1809-1816 (2001).

Tringler, et al., 'B7-H4 is highly expressed in ductal and lobular breast cancer', Clin. Cancer Res., 11(5):1842-1848 (2005).

Tringler, et al., "B7-H4 overexpression in ovarian tumors", Gynecol. Oncol., 100(1):44-52 (2005).

Watanabe, et al., "BTLA is a lymphocyte inhibitory receptor with similarities to CTLA-4 and PD-1", Nature Immunol, 4(7):670-679 (2006).

Zang, et al., "B7x: A widely expressed B7 family member that inhibits T cell activation", Proc. Natl. Acad. Sci. USA, 100(18):10388-10292 (2003).

\* cited by examiner

```
ATGCTGCGTCGGCGGGGCAGCCCTGGCATGGGTGTGCATGTGGGTGCAGCCC
TGGGAGCACTGTGGTTCTGCCTCACAGGAGCCCTGGAGGTCCAGGTCCCTGA
AGACCCAGTGGTGGCACTGGTGGGCACCGATGCCACCCTGTGCTGCTCCTTCT
CCCCTGAGCCTGGCTTCAGCCTGGCACAGCTCAACCTCATCTGGCAGCTGAC
AGATACCAAACAGCTGGTGCACAGCTTTGCTGAGGGCCAGGACCAGGGCAG
CGCCTATGCCAACCGCACGGCCCTCTTCCCGGACCTGCTGGCACAGGGCAAC
GCATCCCTGAGGCTGCAGCGCGTGCGTGTGGCGGACGAGGGCAGCTTCACCT
GCTTCGTGAGCATCCGGGATTTCGGCAGCGCTGCCGTCAGCCTGCAGGTGGC
CGCTCCCTACTCGAAGCCCAGCATGACCCTGGAGCCCAACAAGGACCTGCGG
CCAGGGGACACGGTGACCATCACGTGCTCCAGCTACCGGGGCTACCCTGAGG
CTGAGGTGTTCTGGCAGGATGGGCAGGGTGTGCCCCTGACTGGCAACGTGAC
CACGTCGCAGATGGCCAACGAGCAGGGCTTGTTTGATGTGCACAGCGTCCTG
CGGGTGGTGCTGGGTGCGAATGGCACCTACAGCTGCCTGGTGCGCAACCCCG
TGCTGCAGCAGGATGCGCACGGCTCTGTCACCATCACAGGGCAGCCTATGAC
ATTCCCCCAGAGGCCCTGTGGGTGACCGTGGGGCTGTCTGTCTGTCTCATTG
CACTGCTGGTGGCCCTGGCTTTCGTGTGCTGGAGAAAGATCAAACAGAGCTG
TGAGGAGGAGAATGCAGGAGCTGAGGACCAGGATGGGGAGGGAGAAGGCTC
CAAGACAGCCCTGCAGCCTCTGAAACACTCTGACAGCAAAGAAGATGATGG
ACAAGAAATAGCCTGA
```

FIG. 1

```
ATGCTGCGTCGGCGGGGCAGCCCTGGCATGGGTGTGCATGTGGGTGCAGCCC
TGGGAGCACTGTGGTTCTGCCTCACAGGAGCCCTGGAGGTCCAGGTCCCTGA
AGACCCAGTGGTGGCACTGGTGGGCACCGATGCCACCCTGTGCTGCTCCTTCT
CCCCTGAGCCTGGCTTCAGCCTGGCACAGCTCAACCTCATCTGGCAGCTGAC
AGATACCAAACAGCTGGTGCACAGCTTTGCTGAGGGCCAGGACCAGGGCAG
CGCCTATGCCAACCGCACGGCCCTCTTCCCGGACCTGCTGGCACAGGGCAAC
GCATCCCTGAGGCTGCAGCGCGTGCGTGTGGCGGACGAGGGCAGCTTCACCT
GCTTCGTGAGCATCCGGGATTTCGGCAGCGCTGCCGTCAGCCTGCAGGTGGC
CGCTCCCTACTCGAAGCCCAGCATGACCCTGGAGCCCAACAAGGACCTGCGG
CCAGGGGACACGGTGACCATCACGTGCCCAGCTACCGGGGCTACCCTGAGG
CTGAGGTGTTCTGGCAGGATGGGCAGGGTGTGCCCCTGACTGGCAACGTGAC
CACGTCGCAGATGGCCAACGAGCAGGGCTTGTTTGATGTGCACAGCGTCCTG
CGGGTGGTGCTGGGTGCGAATGGCACCTACAGCTGCCTGGTGCGCAACCCCG
TGCTGCAGCAGGATGCGCACGGCTCTGTCACCATCACAGGGCAGCCTATGAC
ATTCCCCCAGAGGCCCTGTGGGTGACCGTGGGGCTGTCTGTCTGTCTCATTG
CACTGCTGGTGGCCCTGGCTTTCGTGTGCTGGAGAAAGATCAAACAGAGCTG
TGAGGAGGAGAATGCAGGAGCTGAGGACCAGGATGGGGAGGGAGAAGGCTC
CAAGACAGCCCTGCAGCCTCTGAAACACTCTGACAGCAAAGAAGATGATGG
ACAAGAAATAGCCTGA
```

FIG. 2

MLRRRGSPGMGVHVGAALGALWFCLTGALEVQVPEDPVVALVGTDATLCCSFS
PEPGFSLAQLNLIWQLTDTKQLVHSFAEGQDQGSAYANRTALFPDLLAQGNASL
RLQRVRVADEGSFTCFVSIRDFGSAAVSLQVAAPYSKPSMTLEPNKDLRPGDTVT
ITCSSYRGYPEAEVFWQDGQGVPLTGNVTTSQMANEQGLFDVHSVLRVVLGAN
GTYSCLVRNPVLQQDAHGSVTITGQPMTFPPEALWVTVGLSVCLIALLVALAFV
CWRKIKQSCEEENAGAEDQDGEGEGSKTALQPLKHSDSKEDDGQEIA

FIG. 3

MLRRRGSPGMGVHVGAALGALWFCLTGALEVQVPEDPVVALVGTDATLCCSFS
PEPGFSLAQLNLIWQLTDTKQLVHSFAEGQDQGSAYANRTALFPDLLAQGNASL
RLQRVRVADEGSFTCFVSIRDFGSAAVSLQVAAPYSKPSMTLEPNKDLRPGDTVT
ITCPSYRGYPEAEVFWQDGQGVPLTGNVTTSQMANEQGLFDVHSVLRVVLGAN
GTYSCLVRNPVLQQDAHGSVTITGQPMTFPPEALWVTVGLSVCLIALLVALAFV
CWRKIKQSCEEENAGAEDQDGEGEGSKTALQPLKHSDSKEDDGQEIA

FIG. 4

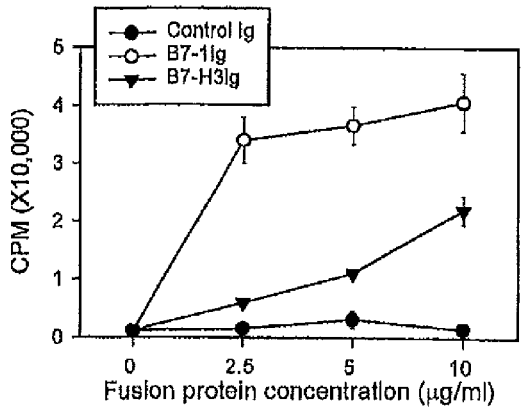

FIG. 8A

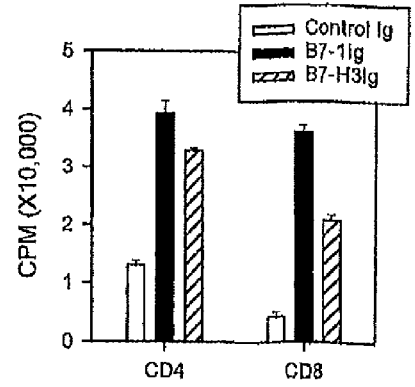

FIG. 8B

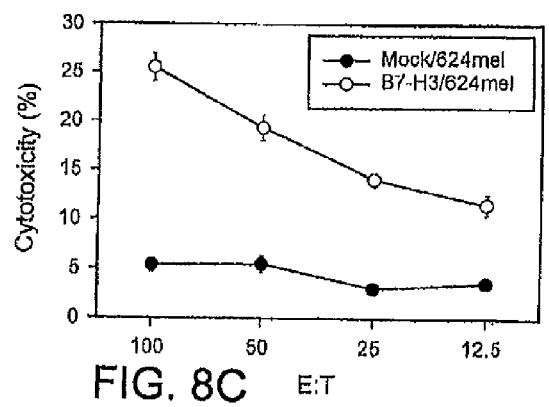

*signal peptide*
MLRRRGSPGMGVHVGAALGALWFCLTGALEVQVPEDPVVALVGTDATLCCSFSPEPGFSLAQLNLIWQLTDTKQLVHSFAEGQDGSAY

*IgV-like domain*
ANRTALFPDLLAQGNASLRLQRVRVADEGSFTCFVSIRDFGSAAVSLQVAAPYSKPSMTLEPNKDLRPGDTVTITTCSSYRGYPEAEVFW

*TM*
QDGQGVPLTGNVTTSQMANEQGLFDVHSVLRVVLGANGTYSCLVRNPVLQQDAHGSVTITGQPMTFPPEALWTVGLSVCLIALLVALA

*IgC-like domain*

*IC*
FVCWRKIKQSCEEENAGAEDQDGEGEGSKTALQPLKHSDSKEDDGQEIA

FIG. 5B

ATGGCTTCCCTGGGGCAGATCCTCTTCTGGAGCATAATTAGCATCATCATTAT
TCTGGCTGGAGCAATTGCACTCATCATTGGCTTTGGTATTTCAGGGAGACACT
CCATCACAGTCACTACTGTCGCCTCAGCTGGGAACATTGGGGAGGATGGAAT
CCTGAGCTGCACTTTTGAACCTGACATCAAACTTTCTGATATCGTGATACAAT
GGCTGAAGGAAGGTGTTTAGGCTTGGTCCATGAGTTCAAAGAAGGCAAAGA
TGAGCTGTCGGAGCAGGATGAAATGTTCAGAGGCCGGACAGCAGTGTTTGCT
GATCAAGTGATAGTTGGCAATGCCTCTTTGCGGCTGAAAAACGTGCAACTCA
CAGATGCTGGCACCTACAAATGTTATATCATCACTTCTAAAGGCAAGGGGAA
TGCTAACCTTGAGTATAAAACTGGAGCCTTCAGCATGCCGGAAGTGAATGTG
GACTATAATGCCAGCTCAGAGACCTTGCGGTGTGAGGCTCCCCGATGGTTCC
CCCAGCCCACAGTGGTCTGGGCATCCCAAGTTGACCAGGGAGCCAACTTCTC
GGAAGTCTCCAATACCAGCTTTGAGCTGAACTCTGAGAATGTGACCATGAAG
GTTGTGTCTGTGCTCTACAATGTTACGATCAACAACACATACTCCTGTATGAT
TGAAAATGACATTGCCAAAGCAACAGGGGATATCAAAGTGACAGAATCGGA
GATCAAAAGGCGGAGTCACCTACAGCTGCTAAACTCAAAGGCTTCTCTGTGT
GTCTCTTCTTTCTTTGCCATCAGCTGGGCACTTCTGCCTCTCAGCCCTTACCT
GATGCTAAAATAA

FIG. 9

MASLGQILFWSIISIIILAGAIALIIGFGISGRHSITVTTVASAGNIGEDGILSCTFEPD
IKLSDIVIQWLKEGVLGLVHEFKEGKDELSEQDEMFRGRTAVFADQVIVGNASLR
LKNVQLTDAGTYKCYIITSKGKGNANLEYKTGAFSMPEVNVDYNASSETLRCEA
PRWFPQPTVVWASQVDQGANFSEVSNTSFELNSENVTMKVVSVLYNVTINNTYS
CMIENDIAKATGDIKVTESEIKRRSHLQLLNSKASLCVSSFFAISWALLPLSPYLM
LK

FIG. 10

FIG. 11

SEQUENCE LISTING

<160> NUMBER OF SEQ ID NOS: 23

<210> SEQ ID NO 1
<211> LENGTH: 316
<212> TYPE: PRT
<213> ORGANISM: Homo sapiens

<400> SEQUENCE: 1

```
Met Leu Arg Arg Arg Gly Ser Pro Gly Met Gly Val His Val Gly Ala
 1               5                  10                  15

Ala Leu Gly Ala Leu Trp Phe Cys Leu Thr Gly Ala Leu Glu Val Gln
                20                  25                  30

Val Pro Glu Asp Pro Val Val Ala Leu Val Gly Thr Asp Ala Thr Leu
            35                  40                  45

Cys Cys Ser Phe Ser Pro Glu Pro Gly Phe Ser Leu Ala Gln Leu Asn
        50                  55                  60

Leu Ile Trp Gln Leu Thr Asp Thr Lys Gln Leu Val His Ser Phe Ala
 65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Arg Gly Tyr Pro Glu Ala Glu Val
                165                 170                 175

Phe Trp Gln Asp Gly Gln Gly Val Pro Leu Thr Gly Asn Val Thr Thr
            180                 185                 190
```

```
Ser Gln Met Ala Asn Glu Gln Gly Leu Phe Asp Val His Ser Val Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Gly Ser Val Thr Ile Thr Gly Gln
225                 230                 235                 240

Pro Met Thr Phe Pro Pro Glu Ala Leu Trp Val Thr Gly Leu Ser
                245                 250                 255

Val Cys Leu Ile Ala Leu Leu Val Ala Leu Ala Phe Val Cys Trp Arg
            260                 265                 270

Lys Ile Lys Gln Ser Cys Glu Glu Asn Ala Gly Ala Glu Asp Gln
                275                 280                 285

Asp Gly Glu Gly Glu Gly Ser Lys Thr Ala Leu Gln Pro Leu Lys His
        290                 295                 300

Ser Asp Ser Lys Glu Asp Asp Gly Gln Glu Ile Ala
305                 310                 315
```

<210> SEQ ID NO 2
<211> LENGTH: 951
<212> TYPE: DNA
<213> ORGANISM: Homo sapiens

<400> SEQUENCE: 2

```
atgctgcgtc ggcggggcag ccctggcatg ggtgtgcatg tgggtgcagc cctgggagca      60
ctgtggttct gcctcacagg agccctggag gtccaggtcc ctgaagaccc agtggtggca     120
ctggtgggca ccgatgccac cctgtgctgc tccttctccc ctgagcctgg cttcagcctg     180
gcacagctca acctcatctg gcagctgaca gataccaaac agctggtgca cagctttgct     240
gagggccagg accagggcag cgcctatgcc aaccgcacgg ccctcttccc ggacctgctg     300
gcacagggca acgcatccct gaggctgcag cgcgtgcgtg tggcggacga gggcagcttc     360
acctgcttcg tgagcatccg ggatttcggc agcgctgccg tcagcctgca ggtggccgct     420
ccctactcga agcccagcat gaccctggag cccaacaagg acctgcggcc aggggacacg     480
gtgaccatca cgtgctccag ctaccggggc taccctgagg ctgaggtgtt ctggcaggat     540
gggcagggtg tgccccctgac tggcaacgtg accacgtcgc agatggccaa cgagcagggc     600
ttgtttgatg tgcacagcgt cctgcgggtg gtgctgggtg cgaatggcac ctacagctgc     660
ctggtgcgca accccgtgct gcagcaggat gcgcacggct ctgtcaccat cacagggcag     720
cctatgacat tccccccaga ggccctgtgg gtgaccgtgg gctgtctgt ctgtctcatt     780
gcactgctgg tggccctggc tttcgtgtgc tggagaaaga tcaaacagag ctgtgaggag     840
gagaatgcag gagctgagga ccaggatggg gagggagaag gctccaagac agccctgcag     900
cctctgaaac actctgacag caaagaagat gatggacaag aaatagcctg a              951
```

<210> SEQ ID NO 3
<211> LENGTH: 316
<212> TYPE: PRT
<213> ORGANISM: Homo sapiens

<400> SEQUENCE: 3

```
Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45
```

Cys Cys Ser Phe Ser Pro Glu Pro Gly Phe Ser Leu Ala Gln Leu Asn
            50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
130                 135                 140

Pro Ser Met Thr Leu Glu Pro Asn Lys Asp Leu Arg Pro Gly Asp Thr
145                 150                 155                 160

Val Thr Ile Thr Cys Pro Ser Tyr Arg Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Val Leu
        195                 200                 205

Arg Val Val Leu Gly Ala Asn Gly Thr Tyr Ser Cys Leu Val Arg Asn
210                 215                 220

Pro Val Leu Gln Gln Asp Ala His Gly Ser Val Thr Ile Thr Gly Gln
225                 230                 235                 240

Pro Met Thr Phe Pro Pro Glu Ala Leu Trp Val Thr Val Gly Leu Ser
                245                 250                 255

Val Cys Leu Ile Ala Leu Leu Val Ala Leu Ala Phe Val Cys Trp Arg
            260                 265                 270

Lys Ile Lys Gln Ser Cys Glu Glu Asn Ala Gly Ala Glu Asp Gln
        275                 280                 285

Asp Gly Glu Gly Glu Gly Ser Lys Thr Ala Leu Gln Pro Leu Lys His
290                 295                 300

Ser Asp Ser Lys Glu Asp Asp Gly Gln Glu Ile Ala
305                 310                 315

<210> SEQ ID NO 4
<211> LENGTH: 951
<212> TYPE: DNA
<213> ORGANISM: Homo sapiens

<400> SEQUENCE: 4
atgctgcgtc ggcgggggcag ccctggcatg ggtgtgcatg tgggtgcagc cctgggagca      60
ctgtggttct gcctcacagg agccctggag gtccaggtcc ctgaagaccc agtggtggca     120
ctggtgggca ccgatgccac cctgtgctgc tccttctccc tgagcctggc ttcagcctg      180 gcacagctca acctcatctg cagctgacag ataccaaaca gctggtgca cagctttgct     240 gagggccagg accagggcag cgcctatgcc aaccgcacgg ccctcttccc ggacctgctg     300
gcacagggca acgcatccct gaggctgcag cgcgtgcgtg tggcggacga gggcagcttc     360
acctgcttcg tgagcatccg ggatttcggc agcgctgccg tcagcctgca ggtggccgct     420
ccctactcga agcccagcat gaccctggag cccaacaagg acctgcggcc aggggacacg     480
gtgaccatca cgtgccccag ctaccggggc taccctgagg ctgaggtgtt ctggcaggat     540
gggcagggtg tgcccctgac tggcaacgtg accacgtcgc agatggccaa cgagcagggc     600

```
ttgtttgatg tgcacagcgt cctgcgggtg gtgctgggtg cgaatggcac ctacagctgc      660
ctggtgcgca accccgtgct gcagcaggat gcgcacggct ctgtcaccat cacagggcag      720
cctatgacat tcccccccaga ggccctgtgg gtgaccgtgg ggctgtctgt ctgtctcatt     780
gcactgctgg tggccctggc tttcgtgtgc tggagaaaga tcaaacagag ctgtgaggag      840
gagaatgcag gagctgagga ccaggatggg gagggagaag ctccaagac agccctgcag       900 cctctgaaac actctgacag caaagaagat gatggacaag aaatagcctg a               951
```

<210> SEQ ID NO 5
<211> LENGTH: 282
<212> TYPE: PRT
<213> ORGANISM: Homo sapiens

<400> SEQUENCE: 5

```
Met Ala Ser Leu Gly Gln Ile Leu Phe Trp Ser Ile Ile Ser Ile Ile
 1               5                  10                  15

Ile Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys
        275                 280
```

<210> SEQ ID NO 6
<211> LENGTH: 849
<212> TYPE: DNA
<213> ORGANISM: Homo sapiens -continued

```
<400> SEQUENCE: 6
atggcttccc tggggcagat cctcttctgg agcataatta gcatcatcat tattctggct    60
ggagcaattg cactcatcat tggctttggt atttcaggga gacactccat cacagtcact   120
actgtcgcct cagctgggaa cattggggag gatggaatcc tgagctgcac ttttgaacct   180
gacatcaaac tttctgatat cgtgatacaa tggctgaagg aaggtgtttt aggcttggtc   240
catgagttca agaaggcaa agatgagctg tcggagcagg atgaaatgtt cagaggccgg   300
acagcagtgt tgctgatca agtgatagtt ggcaatgcct ctttgcggct gaaaaacgtg   360
caactcacag atgctggcac ctacaaatgt tatatcatca cttctaaagg caagggaat   420 gctaaccttg agtataaaac tggagccttc agcatgccgg aagtgaatgt ggactataat   480
gccagctcag agaccttgcg tgtgaggct ccccgatggt tcccccagcc cacagtggtc   540
tgggcatccc aagttgacca gggagccaac ttctcggaag tctccaatac cagctttgag   600
ctgaactctg agaatgtgac catgaaggtt gtgtctgtgc tctacaatgt tacgatcaac   660
aacacatact cctgtatgat tgaaaatgac attgccaaag caacagggga tatcaaagtg   720
acagaatcgg agatcaaaag gcggagtcac ctacagctgc taaactcaaa ggcttctctg   780
tgtgtctctt ctttctttgc catcagctgg gcacttctgc ctctcagccc ttacctgatg   840
ctaaaataa                                                           849
```

<210> SEQ ID NO 7  
<211> LENGTH: 25  
<212> TYPE: PRT  
<213> ORGANISM: Homo sapiens

<400> SEQUENCE: 7

```
Met Ala Ile Ser Gly Val Pro Val Leu Gly Phe Phe Ile Ile Ala Val
 1               5                  10                  15

Leu Met Ser Ala Gln Glu Ser Trp Ala
             20                  25
```

<210> SEQ ID NO 8  
<211> LENGTH: 5  
<212> TYPE: PRT  
<213> ORGANISM: Bos taurus

<400> SEQUENCE: 8

```
Lys Phe Glu Arg Gln
 1               5
```

<210> SEQ ID NO 9  
<211> LENGTH: 15  
<212> TYPE: PRT  
<213> ORGANISM: Homo sapiens

<400> SEQUENCE: 9

```
Met Asp Asp Gln Arg Asp Leu Ile Ser Asn Asn Glu Gln Leu Pro
 1               5                  10                  15
```

<210> SEQ ID NO 10  
<211> LENGTH: 4  
<212> TYPE: PRT  
<213> ORGANISM: Rattus norvegicus

<400> SEQUENCE: 10

```
Lys Asp Glu Leu
 1
```

```
<210> SEQ ID NO 11
<211> LENGTH: 241
<212> TYPE: PRT
<213> ORGANISM: Homo sapiens

<400> SEQUENCE: 11

Leu Arg Ala Asp Thr Gln Glu Lys Glu Val Arg Ala Met Val Gly Ser
  1               5                  10                  15

Asp Val Glu Leu Ser Cys Ala Cys Pro Glu Gly Ser Arg Phe Asp Leu
             20                  25                  30

Asn Asp Val Tyr Val Tyr Trp Gln Thr Ser Glu Ser Lys Thr Val Val
         35                  40                  45

Thr Tyr His Ile Pro Gln Asn Ser Ser Leu Glu Asn Val Asp Ser Arg
     50                  55                  60

Tyr Arg Asn Arg Ala Leu Met Ser Pro Ala Gly Met Leu Arg Gly Asp
 65                  70                  75                  80

Phe Ser Leu Arg Leu Phe Asn Val Thr Pro Gln Asp Glu Gln Lys Phe
                 85                  90                  95

His Cys Leu Val Leu Ser Gln Ser Leu Gly Phe Gln Glu Val Leu Ser
            100                 105                 110

Ile Glu Val Thr Leu His Val Ala Ala Asn Phe Ser Val Pro Val Val
        115                 120                 125

Ser Ala Pro His Ser Pro Ser Gln Asp Glu Leu Thr Phe Thr Cys Thr
    130                 135                 140

Ser Ile Asn Gly Tyr Pro Arg Pro Asn Val Tyr Trp Ile Asn Lys Thr
145                 150                 155                 160

Asp Asn Ser Leu Leu Asp Gln Ala Leu Gln Asn Asp Thr Val Phe Leu
                165                 170                 175

Asn Met Arg Gly Leu Tyr Asp Val Val Ser Val Leu Arg Ile Ala Arg
            180                 185                 190

Thr Pro Ser Val Asn Ile Gly Cys Cys Ile Glu Asn Val Leu Leu Gln
        195                 200                 205

Gln Asn Leu Thr Val Gly Ser Gln Thr Gly Asn Asp Ile Gly Glu Arg
    210                 215                 220

Asp Lys Ile Thr Glu Asn Pro Val Ser Thr Gly Glu Lys Asn Ala Ala
225                 230                 235                 240

Thr

<210> SEQ ID NO 12
<211> LENGTH: 24
<212> TYPE: PRT
<213> ORGANISM: Homo sapiens

<400> SEQUENCE: 12

Tyr Ser Lys Pro Ser Met Thr Leu Glu Pro Asn Lys Asp Leu Arg Pro
  1               5                  10                  15

Gly Asp Thr Val Thr Ile Thr Cys
             20

<210> SEQ ID NO 13
<211> LENGTH: 24
<212> TYPE: PRT
<213> ORGANISM: Homo sapiens

<400> SEQUENCE: 13

Ser Ser Tyr Arg Gly Tyr Pro Glu Ala Glu Val Phe Trp Gln Asp Gly
  1               5                  10                  15

Gln Gly Val Pro Leu Thr Gly Asn
```

```
<210> SEQ ID NO 14
<211> LENGTH: 25
<212> TYPE: PRT
<213> ORGANISM: Homo sapiens

<400> SEQUENCE: 14

Arg Asn Pro Val Leu Gln Gln Asp Ala His Gly Ser Val Thr Ile Thr
 1               5                  10                  15

Gly Gln Pro Met Thr Phe Pro Pro Glu
                20                  25

<210> SEQ ID NO 15
<211> LENGTH: 288
<212> TYPE: PRT
<213> ORGANISM: Homo sapiens

<400> SEQUENCE: 15

Met Gly His Thr Arg Arg Gln Gly Thr Ser Pro Ser Lys Cys Pro Tyr
 1               5                  10                  15

Leu Asn Phe Phe Gln Leu Leu Val Leu Ala Gly Leu Ser His Phe Cys
                20                  25                  30

Ser Gly Val Ile His Val Thr Lys Glu Val Lys Glu Val Ala Thr Leu
            35                  40                  45

Ser Cys Gly His Asn Val Ser Val Glu Glu Leu Ala Gln Thr Arg Ile
 50                  55                  60

Tyr Trp Gln Lys Glu Lys Lys Met Val Leu Thr Met Met Ser Gly Asp
 65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
                100                 105                 110

Thr Tyr Glu Cys Val Val Leu Lys Tyr Glu Lys Asp Ala Phe Lys Arg
            115                 120                 125

Glu His Leu Ala Glu Val Thr Leu Ser Val Lys Ala Asp Phe Pro Thr
130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
                180                 185                 190

Pro Glu Thr Glu Leu Tyr Ala Val Ser Ser Lys Leu Asp Phe Asn Met
            195                 200                 205

Thr Thr Asn His Ser Phe Met Cys Leu Ile Lys Tyr Gly His Leu Arg
210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
                260                 265                 270

Glu Arg Arg Arg Asn Glu Arg Leu Arg Arg Glu Ser Val Arg Pro Val
            275                 280                 285

<210> SEQ ID NO 16
```

<211> LENGTH: 323
<212> TYPE: PRT
<213> ORGANISM: Homo sapiens

<400> SEQUENCE: 16

```
Met Gly Leu Ser Asn Ile Leu Phe Val Met Ala Phe Leu Leu Ser Gly
  1               5                  10                  15

Ala Ala Pro Leu Lys Ile Gln Ala Tyr Phe Asn Glu Thr Ala Asp Leu
             20                  25                  30

Pro Cys Gln Phe Ala Asn Ser Gln Asn Gln Ser Leu Ser Glu Leu Val
         35                  40                  45

Val Phe Trp Gln Asp Gln Glu Asn Leu Val Leu Asn Glu Val Tyr Leu
     50                  55                  60

Gly Lys Glu Lys Phe Asp Ser Val His Ser Lys Tyr Met Gly Arg Thr
 65                  70                  75                  80

Ser Phe Asp Ser Asp Ser Trp Thr Leu Arg Leu His Asn Leu Gln Ile
                 85                  90                  95

Lys Asp Lys Gly Leu Tyr Gln Cys Ile Ile His His Lys Lys Pro Thr
            100                 105                 110

Gly Met Ile Arg Ile His Gln Met Asn Ser Glu Leu Ser Val Leu Ala
        115                 120                 125

Asn Phe Ser Gln Pro Glu Ile Val Pro Ile Ser Asn Ile Thr Glu Asn
130                 135                 140

Val Tyr Ile Asn Leu Thr Cys Ser Ser Ile His Gly Tyr Pro Glu Pro
145                 150                 155                 160

Lys Lys Met Ser Val Leu Leu Arg Thr Lys Asn Ser Thr Ile Glu Tyr
                165                 170                 175

Asp Gly Ile Met Gln Lys Ser Gln Asp Asn Val Thr Glu Leu Tyr Asp
            180                 185                 190

Val Ser Ile Ser Leu Ser Val Ser Phe Pro Asp Val Thr Ser Asn Met
        195                 200                 205

Thr Ile Phe Cys Ile Leu Glu Thr Asp Lys Thr Arg Leu Leu Ser Ser
    210                 215                 220

Pro Phe Ser Ile Glu Leu Glu Asp Pro Gln Pro Pro Pro Asp His Ile
225                 230                 235                 240

Pro Trp Ile Thr Ala Val Leu Pro Thr Val Ile Ile Cys Val Met Val
                245                 250                 255

Phe Cys Leu Ile Leu Trp Lys Trp Lys Lys Lys Arg Pro Arg Asn
            260                 265                 270

Ser Tyr Lys Cys Gly Thr Asn Thr Met Glu Arg Glu Glu Ser Glu Gln
        275                 280                 285

Thr Lys Lys Arg Glu Lys Ile His Ile Pro Glu Arg Ser Asp Glu Ala
    290                 295                 300

Gln Arg Val Phe Lys Ser Ser Lys Thr Ser Ser Cys Asp Lys Ser Asp
305                 310                 315                 320

Thr Cys Phe
```

<210> SEQ ID NO 17
<211> LENGTH: 290
<212> TYPE: PRT
<213> ORGANISM: Homo sapiens

<400> SEQUENCE: 17

```
Met Arg Ile Phe Ala Val Phe Ile Phe Met Thr Tyr Trp His Leu Leu
  1               5                  10                  15

Asn Ala Phe Thr Val Thr Val Pro Lys Asp Leu Tyr Val Val Glu Tyr
```

```
                    20                  25                  30
Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
            85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
            130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
            165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
            195                 200                 205

Cys Thr Phe Arg Arg Leu Asp Pro Glu Glu Asn His Thr Ala Glu Leu
            210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
            245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
            275                 280                 285

Glu Thr
    290

<210> SEQ ID NO 18
<211> LENGTH: 302
<212> TYPE: PRT
<213> ORGANISM: Homo sapiens

<400> SEQUENCE: 18

Met Arg Leu Gly Ser Pro Gly Leu Leu Phe Leu Leu Phe Ser Ser Leu
1               5                   10                  15

Arg Ala Asp Thr Gln Glu Lys Glu Val Arg Ala Met Val Gly Ser Asp
            20                  25                  30

Val Glu Leu Ser Cys Ala Cys Pro Glu Gly Ser Arg Phe Asp Leu Asn
            35                  40                  45

Asp Val Tyr Val Tyr Trp Gln Thr Ser Glu Ser Lys Thr Val Val Thr
50                  55                  60

Tyr His Ile Pro Gln Asn Ser Ser Leu Glu Asn Val Asp Ser Arg Tyr
65                  70                  75                  80

Arg Asn Arg Ala Leu Met Ser Pro Ala Gly Met Leu Arg Gly Asp Phe
            85                  90                  95

Ser Leu Arg Leu Phe Asn Val Thr Pro Gln Asp Glu Gln Lys Phe His
```

-continued

```
                    100                 105                 110
    Cys Leu Val Leu Ser Gln Ser Leu Gly Phe Gln Glu Val Leu Ser Ile
                115                 120                 125

Glu Val Thr Leu His Val Ala Ala Asn Phe Ser Val Pro Val Val Ser
                130                 135                 140

Ala Pro His Ser Pro Ser Gln Asp Glu Leu Thr Phe Thr Cys Thr Ser
    145                 150                 155                 160

Ile Asn Gly Tyr Pro Arg Pro Asn Val Tyr Trp Ile Asn Lys Thr Asp
                    165                 170                 175

Asn Ser Leu Leu Asp Gln Ala Leu Gln Asn Asp Thr Val Phe Leu Asn
                180                 185                 190

Met Arg Gly Leu Tyr Asp Val Ser Val Leu Arg Ile Ala Arg Thr
                195                 200                 205

Pro Ser Val Asn Ile Gly Cys Cys Ile Glu Asn Val Leu Leu Gln Gln
                210                 215                 220

Asn Leu Thr Val Gly Ser Gln Thr Gly Asn Asp Ile Gly Glu Arg Asp
    225                 230                 235                 240

Lys Ile Thr Glu Asn Pro Val Ser Thr Gly Glu Lys Asn Ala Ala Thr
                    245                 250                 255

Trp Ser Ile Leu Ala Val Leu Cys Leu Leu Val Val Ala Val Ala
                260                 265                 270

Ile Gly Trp Val Cys Arg Asp Arg Cys Leu Gln His Ser Tyr Ala Gly
                275                 280                 285

Ala Trp Ala Val Ser Pro Glu Thr Glu Leu Thr Gly His Val
                290                 295                 300

<210> SEQ ID NO 19
<211> LENGTH: 227
<212> TYPE: PRT
<213> ORGANISM: Homo sapiens

<400> SEQUENCE: 19

Ile Ser Gly Arg His Ser Ile Thr Val Thr Thr Val Ala Ser Ala Gly
    1               5                   10                  15

Asn Ile Gly Glu Asp Gly Ile Leu Ser Cys Thr Phe Glu Pro Asp Ile
                20                  25                  30

Lys Leu Ser Asp Ile Val Ile Gln Trp Leu Lys Glu Gly Val Leu Gly
                35                  40                  45

Leu Val His Glu Phe Lys Glu Gly Lys Asp Glu Leu Ser Glu Gln Asp
                50                  55                  60

Glu Met Phe Arg Gly Arg Thr Ala Val Phe Ala Asp Gln Val Ile Val
    65                  70                  75                  80

Gly Asn Ala Ser Leu Arg Leu Lys Asn Val Gln Leu Thr Asp Ala Gly
                    85                  90                  95

Thr Tyr Lys Cys Tyr Ile Ile Thr Ser Lys Gly Lys Gly Asn Ala Asn
                100                 105                 110

Leu Glu Tyr Lys Thr Gly Ala Phe Ser Met Pro Glu Val Asn Val Asp
                115                 120                 125

Tyr Asn Ala Ser Ser Glu Thr Leu Arg Cys Glu Ala Pro Arg Trp Phe
                130                 135                 140

Pro Gln Pro Thr Val Val Trp Ala Ser Gln Val Asp Gln Gly Ala Asn
    145                 150                 155                 160

Phe Ser Glu Val Ser Asn Thr Ser Phe Glu Leu Asn Ser Glu Asn Val
                    165                 170                 175

Thr Met Lys Val Val Ser Val Leu Tyr Asn Val Thr Ile Asn Asn Thr
```

```
                    180                 185                 190
Tyr Ser Cys Met Ile Glu Asn Asp Ile Ala Lys Ala Thr Gly Asp Ile
            195                 200                 205

Lys Val Thr Glu Ser Glu Ile Lys Arg Arg Ser His Leu Gln Leu Leu
210                 215                 220

Asn Ser Lys
225

<210> SEQ ID NO 20
<211> LENGTH: 215
<212> TYPE: PRT
<213> ORGANISM: Homo sapiens

<400> SEQUENCE: 20

Gln Val Pro Glu Asp Pro Val Val Ala Leu Val Gly Thr Asp Ala Thr
1               5                   10                  15

Leu Cys Cys Ser Phe Ser Pro Glu Pro Gly Phe Ser Leu Ala Gln Leu
            20                  25                  30

Asn Leu Ile Trp Gln Leu Thr Asp Thr Lys Gln Leu Val His Ser Phe
        35                  40                  45

Ala Glu Gly Gln Asp Gln Gly Ser Ala Tyr Ala Asn Arg Thr Ala Leu
    50                  55                  60

Phe Pro Asp Leu Leu Ala Gln Gly Asn Ala Ser Leu Arg Leu Gln Arg
65                  70                  75                  80

Val Arg Val Ala Asp Glu Gly Ser Phe Thr Cys Phe Val Ser Ile Arg
                85                  90                  95

Asp Phe Gly Ser Ala Ala Val Ser Leu Gln Val Ala Ala Pro Tyr Ser
            100                 105                 110

Lys Pro Ser Met Thr Leu Glu Pro Asn Lys Asp Leu Arg Pro Gly Asp
        115                 120                 125

Thr Val Thr Ile Thr Cys Pro Ser Tyr Arg Gly Tyr Pro Glu Ala Glu
    130                 135                 140

Val Phe Trp Gln Asp Gly Gln Gly Val Pro Leu Thr Gly Asn Val Thr
145                 150                 155                 160

Thr Ser Gln Met Ala Asn Glu Gln Gly Leu Phe Asp Val His Ser Val
                165                 170                 175

Leu Arg Val Val Leu Gly Ala Asn Gly Thr Tyr Ser Cys Leu Val Arg
            180                 185                 190

Asn Pro Val Leu Gln Gln Asp Ala His Gly Ser Val Thr Ile Thr Gly
        195                 200                 205

Gln Pro Met Thr Phe Pro Pro
    210                 215

<210> SEQ ID NO 21
<211> LENGTH: 226
<212> TYPE: PRT
<213> ORGANISM: Homo sapiens

<400> SEQUENCE: 21

Leu Asn Phe Phe Gln Leu Leu Val Leu Ala Gly Leu Ser His Phe Cys
1               5                   10                  15

Ser Gly Val Ile His Val Thr Lys Glu Val Lys Glu Val Ala Thr Leu
            20                  25                  30

Ser Cys Gly His Asn Val Ser Val Glu Glu Leu Ala Gln Thr Arg Ile
        35                  40                  45

Tyr Trp Gln Lys Glu Lys Lys Met Val Leu Thr Met Met Ser Gly Asp
    50                  55                  60
```

Met Asn Ile Trp Pro Glu Tyr Lys Asn Arg Thr Ile Phe Asp Ile Thr
65                  70                  75                  80

Asn Asn Leu Ser Ile Val Ile Leu Ala Leu Arg Pro Ser Asp Glu Gly
                85                  90                  95

Thr Tyr Glu Cys Val Val Leu Lys Tyr Glu Lys Asp Ala Phe Lys Arg
            100                 105                 110

Glu His Leu Ala Glu Val Thr Leu Ser Val Lys Ala Asp Phe Pro Thr
        115                 120                 125

Pro Ser Ile Ser Asp Phe Glu Ile Pro Thr Ser Asn Ile Arg Arg Ile
    130                 135                 140

Ile Cys Ser Thr Ser Gly Gly Phe Pro Glu Pro His Leu Ser Trp Leu
145                 150                 155                 160

Glu Asn Gly Glu Glu Leu Asn Ala Ile Asn Thr Thr Val Ser Gln Asp
                165                 170                 175

Pro Glu Thr Glu Leu Tyr Ala Val Ser Ser Lys Leu Asp Phe Asn Met
            180                 185                 190

Thr Thr Asn His Ser Phe Met Cys Leu Ile Lys Tyr Gly His Leu Arg
        195                 200                 205

Val Asn Gln Thr Phe Asn Trp Asn Thr Thr Lys Gln Glu His Phe Pro
    210                 215                 220

Asp Asn
225

<210> SEQ ID NO 22
<211> LENGTH: 219
<212> TYPE: PRT
<213> ORGANISM: Homo sapiens

<400> SEQUENCE: 22

Gln Ala Tyr Phe Asn Glu Thr Ala Asp Leu Pro Cys Gln Phe Ala Asn
1               5                   10                  15

Ser Gln Asn Gln Ser Leu Ser Glu Leu Val Val Phe Trp Gln Asp Gln
                20                  25                  30

Glu Asn Leu Val Leu Asn Glu Val Tyr Leu Gly Lys Glu Lys Phe Asp
            35                  40                  45

Ser Val His Ser Lys Tyr Met Gly Arg Thr Ser Phe Asp Ser Asp Ser
        50                  55                  60

Trp Thr Leu Arg Leu His Asn Leu Gln Ile Lys Asp Lys Gly Leu Tyr
65                  70                  75                  80

Gln Cys Ile Ile His His Lys Lys Pro Thr Gly Met Ile Arg Ile His
                85                  90                  95

Gln Met Asn Ser Glu Leu Ser Val Leu Ala Asn Phe Ser Gln Pro Glu
            100                 105                 110

Ile Val Pro Ile Ser Asn Ile Thr Glu Asn Val Tyr Ile Asn Leu Thr
        115                 120                 125

Cys Ser Ser Ile His Gly Tyr Pro Glu Pro Lys Lys Met Ser Val Leu
    130                 135                 140

Leu Arg Thr Lys Asn Ser Thr Ile Glu Tyr Asp Gly Ile Met Gln Lys
145                 150                 155                 160

Ser Gln Asp Asn Val Thr Glu Leu Tyr Asp Val Ser Ile Ser Leu Ser
                165                 170                 175

Val Ser Phe Pro Asp Val Thr Ser Asn Met Thr Ile Phe Cys Ile Leu
            180                 185                 190

Glu Thr Asp Lys Thr Arg Leu Leu Ser Ser Pro Phe Ser Ile Glu Leu
        195                 200                 205

```
Glu Asp Pro Gln Pro Pro Pro Asp His Ile Pro
    210                 215

<210> SEQ ID NO 23
<211> LENGTH: 220
<212> TYPE: PRT
<213> ORGANISM: Homo sapiens

<400> SEQUENCE: 23

Val Thr Val Pro Lys Asp Leu Tyr Val Val Glu Tyr Gly Ser Asn Met
1               5                   10                  15

Thr Ile Glu Cys Lys Phe Pro Val Glu Lys Gln Leu Asp Leu Ala Ala
            20                  25                  30

Leu Ile Val Tyr Trp Glu Met Glu Asp Lys Asn Ile Ile Gln Phe Val
            35                  40                  45

His Gly Glu Glu Asp Leu Lys Val Gln His Ser Ser Tyr Arg Gln Arg
    50                  55                  60

Ala Arg Leu Leu Lys Asp Gln Leu Ser Leu Gly Asn Ala Ala Leu Gln
65                  70                  75                  80

Ile Thr Asp Val Lys Leu Gln Asp Ala Gly Val Tyr Arg Cys Met Ile
                85                  90                  95

Ser Tyr Gly Gly Ala Asp Tyr Lys Arg Ile Thr Val Lys Val Asn Ala
            100                 105                 110

Pro Tyr Asn Lys Ile Asn Gln Arg Ile Leu Val Val Asp Pro Val Thr
            115                 120                 125

Ser Glu His Glu Leu Thr Cys Gln Ala Glu Gly Tyr Pro Lys Ala Glu
    130                 135                 140

Val Ile Trp Thr Ser Ser Asp His Gln Val Leu Ser Gly Lys Thr Thr
145                 150                 155                 160

Thr Thr Asn Ser Lys Arg Glu Glu Lys Leu Phe Asn Val Thr Ser Thr
                165                 170                 175

Leu Arg Ile Asn Thr Thr Thr Asn Glu Ile Phe Tyr Cys Thr Phe Arg
            180                 185                 190

Arg Leu Asp Pro Glu Glu Asn His Thr Ala Glu Leu Val Ile Pro Glu
            195                 200                 205

Leu Pro Leu Ala His Pro Pro Asn Glu Arg Thr His
    210                 215                 220
```

B7-H3 AND B7-H4, NOVEL IMMUNOREGULATORY MOLECULES

CROSS-REFERENCE TO RELATED APPLICATIONS

This application is a continuation application of co-pending U.S. application Ser. No. 13/323,360, filed Dec. 12, 2011, which is a divisional application of U.S. application Ser. No. 11/929,481, filed Oct. 30, 2007, now U.S. Pat. No. 8,129,347, issued Mar. 6, 2012, which is a continuation application of U.S. application Ser. No. 11/120,927, filed May 2, 2005, now U.S. Pat. No. 7,622,565, issued Nov. 24, 2009, which is a continuation application of U.S. application Ser. No. 09/915,789, filed Jul. 26, 2001, now U.S. Pat. No. 6,891,030, issued May 10, 2005, which claims priority to U.S. Provisional Application No. 60/220,991, filed Jul. 27, 2000. The disclosures of U.S. application Ser. Nos. 13/323,360, 11/929,481, 11/120,927, 09/915,789, and U.S. Provisional Application No. 60/220,991 are incorporated herein by reference in their entirety.

BACKGROUND OF THE INVENTION

The invention is generally in the field of immunoregulation, and specifically T cell response regulation.

Mammalian *T lymphocytes* recognize antigenic peptides bound to major histocompatibility complex (MHC) molecules on the surface of antigen presenting cells (APC). The antigenic peptides are generated by proteolytic degradation of protein antigens within the APC. The interaction of the T cells with the APC and the subsequent response of the T cells are qualitatively and quantitatively regulated by interactions between cell surface receptors on the T cells with both soluble mediators and ligands on the surface of APC.

SUMMARY OF THE INVENTION

The invention is based on the cloning of three human cDNA molecules encoding three novel polypeptides that co-stimulate T cell responses and on the functional characterization of the polypeptides that the cDNA molecules encode. Two of these novel co-stimulatory polypeptides, the B7-H3 polypeptides, differ from each other by a single amino acid residue (position number 166). The B7-H3 polypeptide with serine at position 166 is designated herein B7-H3.1 (SEQ ID NO:1) and that with proline at position 166 is designated B7-H3.2 (SEQ ID NO:3). Text that refers to B7-H3 without specifying B7-H3.1 or B7-H3.2 is pertinent to both polypeptides. The third novel co-stimulatory polypeptide, B7-H4, is encoded by a separate gene. The invention features DNA molecules encoding the B7-H3 and B7-H4 polypeptides, functional fragments of the polypeptides, and fusion proteins containing the polypeptides or functional fragments of the polypeptides, B7-H3 and B7-H4 and functional fragments of both, vectors containing the DNA molecules, and cells containing the vectors. Also included in the invention are antibodies that bind to the B7-H3 and B7-H4 polypeptides. The invention features in vitro, in vivo, and ex vivo methods of co-stimulating T cell responses, methods of screening for compounds that inhibit or enhance T cell responses, and methods for producing the polypeptides and fusion proteins.

Specifically the invention features an isolated DNA including: (a) a nucleic acid sequence that (i) encodes a polypeptide with the ability to co-stimulate a T cell, and (ii) hybridizes under stringent conditions to the complement of a sequence that encodes a polypeptide with an amino acid sequence with SEQ ID NO:1, or SEQ ID NO:3, or SEQ ID NO:5; or (b) a complement of this nucleic acid sequence. The polypeptide-encoding nucleic acid sequence included in the isolated DNA will be at least 10 bp, 15 bp, 25 bp, 50 bp, 75 bp, 100 bp, 125 bp, 150 bp, 175 bp, 200 bp, 250 bp, 300 bp, 350 bp, 400 bp, 450 bp, 500 bp, 550 bp, 600 bp, 650 bp, 700 bp, 750 bp, 800 bp, 840 bp, 850 bp, 900 bp, or 940 bp long. The nucleic acid sequence can encode a B7-H3 polypeptide that includes an amino acid sequence (a) extending from amino acid 27, 28, 29, 30, 31, 32, 33, or 34 to amino acid 316 of either SEQ ID NO:1 or SEQ ID NO:3, or (b) of SEQ ID NO:1 or SEQ ID NO:3. Alternatively, the nucleic acid sequence can have a nucleotide sequence with SEQ ID NO:2 or SEQ ID NO:4. The nucleic acid sequence can encode a B7-H4 polypeptide that includes an amino acid sequence with SEQ ID NO:5 or it can have a nucleotide sequence with SEQ ID NO:6. The nucleic acid sequence can also encode functional fragments of these B7-H3 or B7-H4 polypeptides.

The invention also embodies an isolated B7-H3 polypeptide encoded by a DNA that includes a nucleic acid sequence that (i) encodes a polypeptide with the ability to co-stimulate a T cell and (ii) hybridizes under stringent conditions to the complement of a sequence that encodes a polypeptide with an amino acid sequence with SEQ ID NO:1 or SEQ ID NO:3. The B7-H3 polypeptide can include an amino acid sequence starting at residue 27, 28, 29, 30, 31, 32, 33 or 34 and extending to 361 of SEQ ID NO:1 or SEQ ID NO:3. The invention also encompasses B7-H3 polypeptides that include an amino acid sequence with SEQ ID NO:1 or SEQ ID NO:3, or either of these amino acid sequences but differing solely by one or more (e.g., two, three, four, five, six, seven, eight, nine, ten, 12, 15, 20, 25, 30, 35, 40, 50, 60, 80, or 100) conservative substitutions.

The invention also includes an isolated B7-H4 polypeptide encoded by DNA that includes a nucleic acid sequence that (i) encodes a polypeptide with the ability to co-stimulate a T cell and (ii) hybridizes under stringent conditions to the complement of a sequence that encodes a polypeptide with an acid sequence with SEQ ID NOS:5. The B7-H4 polypeptide can include an amino acid sequence starting at residue 27, 28, 29, 30, 31, 32, 33, or 34 and extending to residue 282 of SEQ ID NO: 5 or this amino acid sequence but differing solely by one or more (e.g., two, three, four, five, six, seven, eight, nine, ten, 12, 15, 20, 25, 30, 35, 40, 50, 60, 80 or 100) conservative substitutions.

Also encompassed by the invention are functional fragments of any of the above polypeptides.

The polypeptides of the invention include fusion proteins containing a first domain and at least one additional domain. The first domain can be any of the B7-H3 or B7-H4 polypeptides described above or a functional fragment of any of these polypeptides. The at least one additional domain can be a heterologous targeting or leader sequence, an amino acid sequence that facilitates purification, detection, or solubility of the fusion protein. The second domain can be, for example, all or part of an immunoglobulin (Ig) heavy chain constant region. Also included are isolated nucleic acid molecules encoding the fusion proteins.

The invention features vectors containing any of the DNAs of the invention and nucleic acid molecules encoding the fusion proteins of the invention. The vectors can be expression vectors in which the nucleic acid coding sequence or molecule is operably linked to a regulatory element which allows expression of the nucleic acid sequence or molecule in a cell. Also included in the invention are cells (e.g., mammalian, insect, yeast, fungal, or bacterial cells) containing any of the vectors of the invention.

Another embodiment of the invention is a method of co-stimulating a T cell that involves contacting the T cell with any of the B7-H3 or B7-H4 polypeptides of the invention, functional fragments thereof, or fusion proteins of the invention; these 3 classes of molecule are, for convenience, designated "B7-H3 agents" or "B7-H4 agents." The contacting can be by, for example, culturing any of these B7-H3 or B7-H4 agents with the T cell in vitro. Alternatively, the T cell can be in a mammal and the contacting can be by, for example, administering any of the B7-H3 or B7-H4 agents to the mammal or administering a nucleic acid encoding the B7-H3 or B7-H4 agent to the mammal. In addition, the method can be an ex vivo procedure that involves: providing a recombinant cell which is the progeny of a cell obtained from the mammal and has been transfected or transformed ex vivo with a nucleic acid encoding any of the B7-H3 or B7-H4 agents so that the cell expresses the B7-H3 or B7-H4 agent; and administering the cell to the mammal. In this ex vivo procedure, the cell can be an antigen presenting cell (APC) that expresses the B7-H3 agent or B7-H4 agent on its surface. Furthermore, prior to administering to the mammal, the APC can be pulsed with an antigen or an antigenic peptide. In addition, the cell obtained from the mammal can be a tumor cell. In any of these methods of the invention, the B7-H3 or B7-H4 agents can co-stimulate the production of interferon-γ by the T cell.

Also embodied by the invention is a method of co-stimulating a T cell in which the T cell is contacted with: (a) a first co-stimulatory polypeptide that can be either (i) B7-H1, (ii) B7-H2, (iii) B7-H3, (iv) B7-H4, (v) a functional fragment of any of (i)-(iv), or (vi) any of (i)-(v) but with one or more conservative substitutions; and (b) one or more additional co-stimulatory polypeptides that can be either (vi) B7-1, (vii) B7-2, (viii) B7-H1, (ix) B7-H2, (x) B7-H3, (xi) B7-H4, (xii) a functional fragment of any of (vi)-(xi), or (xii) any of (vi) (xii) but with one or more conservative substitutions. The contacting can be by, for example, culturing the first co-stimulatory polypeptide and the one or more additional co-stimulatory polypeptides with the T cell in vitro. Alternatively, the T cell can be in a mammal and the contacting can be by, for example, administering the first co-stimulatory polypeptide and the one or more additional co-stimulatory polypeptides to the mammal. In addition, contacting of a T cell in a mammal can be by administering one or more nucleic acids encoding the first co-stimulatory polypeptide and the one more additional co-stimulatory polypeptides to the mammal. The method can also be an ex vivo procedure that, for example, involves: providing a recombinant cell which is the progeny of a cell obtained from the mammal and which has been transfected or transformed ex vivo with one or more nucleic acids encoding the first co-stimulatory polypeptide and the one or more additional polypeptides so that the cell expresses the first co-stimulatory polypeptide and the one or more additional co-stimulatory polypeptides; and administering the cell to the mammal. Alternatively, the ex vivo procedure can involve: providing a first recombinant cell which is the progeny of a cell obtained from the mammal and which has been transfected or transformed ex vivo with a nucleic acid encoding the first co-stimulatory polypeptide; providing one or more additional recombinant cells each of which is the progeny of a cell obtained from the mammal and each of which has been transfected or transformed ex vivo with a nucleic acid encoding one of the additional one or more co-stimulatory polypeptides; and administering the first cell and the one or more additional cells to the mammal. The recombinant cells used in the any of the ex vivo procedures can be antigen presenting cells (APC) and they can express the first co-stimulatory polypeptide and/or the one or more additional co-stimulatory polypeptides on their surfaces. Prior to the administering, APC can be pulsed with an antigen or an antigenic peptide. In addition, the cell obtained from the mammal can be a tumor cell.

In any of the above methods of co-stimulating a T cell, the mammal can be suspected of having, for example, an immunodeficiency disease, an inflammatory condition, or an autoimmune disease.

The invention includes a method of identifying a compound that inhibits an immune response. The method involves: providing a test compound; culturing, together, the compound, one or more B7-H3 or B7-H4 agents, a T cell, and a T cell activating stimulus; and determining whether the test compound inhibits the response of the T cell to the stimulus, as an indication that the test compound inhibits an immune response. The invention also embodies a method of identifying a compound that enhances an immune response. The method involves: providing a test compound; culturing, together, the compound, one or more of B7-H3 or B7-H4 agents, a T cell, and a T cell activating stimulus; and determining whether the test compound enhances the response of the T cell to the stimulus, as an indication that the test compound enhances an immune response. In both these methods, the stimulus can be, for example, an antibody that binds to a T cell receptor or a CD3 polypeptide. Alternatively, the stimulus can be an alloantigen or an antigenic peptide bound to a major histocompatibility complex (MHC) molecule on the surface of an antigen presenting cell (APC). The APC can be transfected or transformed with a nucleic acid encoding the B7-H3 or B7-H4 agent and the B7-H3 or B7-H4 agent can be expressed on the surface of the APC.

The invention also features an antibody (e.g., a polyclonal or a monoclonal antibody) that binds specifically to one of the B7-H3 or B7-H4 polypeptides of the invention, e.g., the polypeptide with SEQ ID NO:1, SEQ ID NO:3, or SEQ ID NO:5.

The invention also features a method of producing any of the B7-H3 or B7-H4 polypeptides of the invention, functional fragments thereof, or fusion proteins of the invention. The method involves culturing a cell of the invention and purifying the relevant B7-H3 or B7-H4 protein from the culture.

"Polypeptide" and "protein" are used interchangeably and mean any peptide-linked chain of amino acids, regardless of length or post-translational modification. The invention also features B7-H3 and B7-H4 polypeptides with conservative substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

The term "isolated" polypeptide or peptide fragment as used herein refers to a polypeptide or a peptide fragment which either has no naturally-occurring counterpart (e.g., a peptidomimetic), or has been separated or purified from components which naturally accompany it, e.g., in tissues such as pancreas, liver, spleen, ovary, testis, muscle, joint tissue, neural tissue, gastrointestinal tissue, or body fluids such as blood, serum, or urine. Typically, the polypeptide or peptide fragment is considered "isolated" when it is at least 70%, by dry weight, free from the proteins and naturally-occurring organic molecules with which it is naturally associated. Preferably, a preparation of a polypeptide (or peptide fragment thereof) of the invention is at least 80%, more preferably at least 90%, and most preferably at least 99%, by dry weight, the polypeptide (or the peptide fragment thereof), respectively, of the invention. Thus, for example, a preparation of polypeptide x is at least 80%, more preferably at least 90%, and most preferably at least 99%, by dry weight, polypeptide x. Since a polypeptide that is chemically synthesized is, by its nature, separated from the components that naturally accompany it, the synthetic polypeptide or nucleic acid is "isolated."

An isolated polypeptide (or peptide fragment) of the invention can be obtained, for example, by extraction from a natural source (e.g., from human tissues or bodily fluids); by expression of a recombinant nucleic acid encoding the peptide; or by chemical synthesis. A peptide that is produced in a cellular system different from the source from which it naturally originates is "isolated," because it will be separated from components which naturally accompany it. The extent of isolation or purity can be measured by any appropriate method, e.g., column chromatography, polyacrylamide gel electrophoresis, or HPLC analysis.

An "isolated DNA" means DNA free of the genes that flank the gene of interest in the genome of the organism in which the gene of interest naturally occurs. The term therefore includes a recombinant DNA incorporated into a vector, into an autonomously replicating plasmid or virus, or into the genomic DNA of a prokaryote or eukaryote. It also includes a separate molecule such as: a cDNA where the corresponding genomic DNA has introns and therefore a different sequence; a genomic fragment; a fragment produced by polymerase chain reaction (PCR); a restriction fragment; a DNA encoding a non-naturally occurring protein, fusion protein, or fragment of a given protein; or a nucleic acid which is a degenerate variant of a naturally occurring nucleic acid. In addition, it includes a recombinant nucleotide sequence that is part of a hybrid gene, i.e., a gene encoding a fusion protein. Also included is a recombinant DNA that includes a portion of SEQ ID NO:2, SEQ ID NO:4, or SEQ ID NO:6. From the above it will be clear that an isolated DNA does not include a restriction fragment containing all or part of a gene that flanks the gene of interest in the genome of the organism in which the gene of interest naturally occurs. Furthermore, an isolated DNA does not mean a DNA present among hundreds to millions of other DNA molecules within, for example, cDNA or genomic DNA libraries or genomic DNA restriction digests in, for example, a restriction digest reaction mixture or an electrophoretic gel slice.

As used herein, a polypeptide that "co-stimulates" a T cell is a polypeptide that, upon interaction with a cell-surface molecule on the T cell, enhances the response of the T cell. The T cell response that results from the interaction will be greater than the response in the absence of the polypeptide. The response of the T cell in the absence of the co-stimulatory polypeptide can be no response or it can be a response significantly lower than in the presence of the co-stimulatory polypeptide. It is understood that the response of the T cell can an effector, helper, or suppressive response.

As used herein, the term "co-stimulatory" polypeptide or molecule includes molecules such as B7-1, B7-2, B7-H1, B7-H2, B7-H3, B7-H4, 4-1BB, OX40, and herpes virus entry mediator (HVEM). As used herein, an "activating stimulus" is a molecule that delivers an activating signal to a T cell, preferably through the antigen specific T cell receptor (TCR). The activating stimulus can be sufficient to elicit a detectable response in the T cell. Alternatively, the T cell may require co-stimulation (e.g., by a B7-H3 or B7-H4 polypeptide) in order to respond detectably to the activating stimulus. Examples of activating stimuli include, without limitation, antibodies that bind to the TCR or to a polypeptide of the CD3 complex that is physically associated with the TCR on the T cell surface, alloantigens, or an antigenic peptide bound to a MHC molecule.

As used herein, a "fragment" of a B7-H3 or B7-H4 polypeptide is a fragment of the polypeptide that is shorter than the full-length polypeptide. Generally, fragments will be five or more amino acids in length. An antigenic fragment has the ability to be recognized and bound by an antibody.

As used herein, a "functional fragment" of a B7-H3 or B7-H4 polypeptide is a fragment of the polypeptide that is shorter than the full-length polypeptide and has the ability to co-stimulate a T cell. Methods of establishing whether a fragment of an B7-H3 or B7-H4 molecule is functional are known in the art. For example, fragments of interest can be made by either recombinant, synthetic, or proteolytic digestive methods. Such fragments can then be isolated and tested for their ability to co-stimulate T cells by procedures described herein.

As used herein, "operably linked" means incorporated into a genetic construct so that expression control sequences effectively control expression of a coding sequence of interest.

As used herein, the term "antibody" refers not only to whole antibody molecules, but also to antigen-binding fragments, e.g., Fab, F(ab')$_2$, Fv, and single chain Fv fragments. Also included are chimeric antibodies.

As used herein, an antibody that "binds specifically" to an isolated B7-H4 polypeptide encoded by a DNA that includes a nucleic acid sequence that (i) encodes a polypeptide with the ability to co-stimulate a T cell and (ii) hybridizes under stringent conditions to the complement of a sequence that encodes a polypeptide with an amino acid sequence with SEQ ID NO:5, is an antibody that does not bind substantially to B7-1, B7-2, B7-H1, B7-H2, or B7-H3.

As used herein, an antibody that "binds specifically" to an isolated B7-H3 polypeptide that includes an amino acid sequence of amino acid residue 31 to amino acid residue 316 of SEQ ID NO: 3 is an antibody that does not bind substantially to B7-1, B7-2, B7-H1, B7-H2, or B7-H4. In addition, an antibody that binds specifically to B7-H3.1 preferably does not substantially bind to B7-H3.2 and vice versa.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., enhancing immune responses in mammalian subjects, will be apparent from the following description, from the drawings and from the claims.

BRIEF DESCRIPTION OF THE DRAWINGS

FIG. 1 is a depiction of the nucleotide sequence of cDNA encoding B7H-3.1 (SEQ ID NO:2). Nucleotide residue 496 is shown in bold.

FIG. 2 is a depiction of the nucleotide sequence of cDNA encoding B7H-3.2 (SEQ ID NO:4). Nucleotide residue 496 is shown in bold.

FIG. 3 is a depiction of the amino acid sequence of B7-H3.1 (SEQ ID NO:1). Amino acid residue 166 is shown in bold.

FIG. 4 is a depiction of the amino acid sequence of B7-H3.2 (SEQ ID NO:3). Amino acid residue 166 is shown in bold.

FIG. 5A is a depiction of the amino acid sequences of human B7-H3.1 (SEQ ID NO:1), human B7-1 (SEQ ID NO:15), human B7-2 (SEQ ID NO:16), human B7-H1 (SEQ ID NO:17), and human B7-2 (SEQ ID NO:18) aligned for optimal homology. Identical amino acid residues are shaded in bold and conserved amino acid residues are boxed. Conserved cysteine residues are marked *.

FIG. 5B is a depiction of the amino acid sequence of B7-H.3.1 showing the predicted signal peptide (——) IgV-like domain (• • • •) IgC-like domain (— — —), transmembrane domain (▪▪▪▪▪▪) and intracellular tail (— • • — • •). Potential N-glycosylation sites are shown in bold ("N").

FIG. 8A is a line graph showing the proliferative response of nylon wool-purified T cells activated by anti-CD3 mAb (coated onto tissue culture well bottoms using a concentration of 40 ng/ml) and co-stimulated by either control Ig, B7-1Ig fusion protein, or B7-H3Ig fusion protein coated onto the tissue culture well bottoms at the indicated concentrations.

FIG. 8B is a bar graph showing the proliferative responses of purified CD4+ and CD8+ T cells activated by anti-CD3 mAb (coated onto tissue culture well bottoms using a concentration of 40 ng/ml) and co-stimulated by either control Ig, B7-1Ig fusion protein, or B7-H3Ig fusion protein, each coated onto tissue culture well bottoms using a concentration of 10 µg/ml.

FIG. 8C is a line graph showing the cytolytic activity on wild-type 624me1 tumor target cells of cytotoxic T lymphocytes (CTL) (at the indicated effector to target cell ratios ("E:T")) generated by culturing nylon wool-purified T cells with 624me1 tumor cells transfected with either the control parental pcDNA3.1(−) expression vector ("Mock/624me1") or the pcDNA/B7-H3 expression vector containing the B7H-3.1 coding region ("B7-H3/624me1").

FIG. 9 is a depiction of the nucleotide sequence of cDNA encoding B7-H4 (SEQ ID NO:6).

FIG. 10 is a depiction of the amino acid sequence of B7-H4 (SEQ ID NO:5).

FIG. 11 is a depiction of the amino acid sequences of the extracellular domains of human B7-H4 (SEQ ID NO: 19), human B7-H3.2 (SEQ ID NO:20), human B7-1 (SEQ ID NO:21), human B7-2 (SEQ ID NO:22), human B7-H1 (SEQ ID NO:23), and human B7-2 (SEQ ID NO:24) aligned for optimal homology. Identical amino acid residues are shaded in bold and conserved amino acid residues are boxed. Conserved cysteine residues are marked *.

DETAILED DESCRIPTION

Figure 6A:
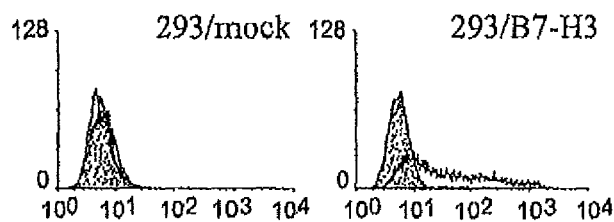
FIG. 6A is a pair of fluorescence flow cytometry histograms showing the staining by an anti-B7-H3 antiserum (open area) or control serum (shaded area) of 293 cells transfected with either the control pcDNA3.1(−) parental vector ("293/mock"; left histogram) or the pcDNA/B7-H3 vector containing the B7H-3.1 coding region ("293/B7-H3"; right histogram).

Using a novel PCR-based strategy, the inventor has identified two cDNA sequences (SEQ ID NOS:2 and 4) corresponding to two alleles of a gene encoding a novel B7-related molecule (B7-H3).

Translation of the cDNA sequences indicated that the two polypeptides (B7-H3.1 and B7-H3.2; SEQ ID NOS:1 and 3, respectively) encoded by the two allelic cDNA molecules are type I transmembrane proteins of 316 amino acids, each containing an immunoglobulin (Ig) V-like domain, Ig C-like domain, a transmembrane domain and a cytoplasmic domain of 30 amino acids. Northern blot analysis showed strong expression of the gene encoding B7-H3 in heart, liver, placenta, prostate, testis, uterus, pancreas, small intestine, and colon, and weak expression in brain, skeletal muscle, kidney, and lung. Expression was undetectable in peripheral blood mononuclear cells (PBMC) but was detectable in spleen, lymph nodes, bone marrow, fetal liver, and thymus.

Fluorescence flow cytometry using an antiserum produced by immunization of mice with a carrier-conjugated peptide corresponding to a hydrophilic region of B7-H3, indicated no expression of B7-H3 on the majority of hematopoietic cells. However, less than 3% of resting CD14+ cells expressed the molecule on their surfaces. Activation with phorbol myristic acid (PMA) and ionomycin increased expression on T cells, monocytes, and dendritic cells.

Binding experiments indicated that T cells express a counter-receptor for B7-H3 that is not CTLA4, ICOS, or CD28.

In vitro experiments with isolated human T cells and a B7-H3.1-containing fusion protein indicated that while B7-H3 had no direct activity on T cells, it enhanced ("co-stimulated") CD4+ and CD8+ T cell proliferative responses induced by antibody specific for human CD3.

Using a strategy similar to that used to clone B7-H3 cDNA, a cDNA molecule containing an open reading frame (orf)

encoding another B7 homologue (B7-H4) was cloned, the nucleotide sequence of the off (SEQ ID NO:6) was obtained, and the amino acid sequence of the encoded sequence (SEQ ID NO:5) was derived. B7-H4 is a type I transmembrane protein of 282 amino acids and has the same domain structure as B7-H3. Northern blot analysis showed expression of B7-H4 in lymphoid organs such as spleen and thymus. Binding experiments showed that there is a counter-receptor for B7-H4 on activated but not resting T cells. B7-H4, like B7-H3, co-stimulated T cell proliferation.

B7-H3 and B7-H4 can be used as augmenters of immune responses both in vivo and in vitro.

Nucleic Acid Molecules

The B7-H3 and B7-H4 nucleic acid molecules of the invention can be cDNA, genomic DNA, synthetic DNA, or RNA, and can be double-stranded or single-stranded (i.e., either a sense or an antisense strand). Fragments of these molecules are also considered within the scope of the invention, and can be produced by, for example, the polymerase chain reaction (PCR) or generated by treatment with one or more restriction endonucleases. A ribonucleic acid (RNA) molecule can be produced by in vitro transcription. Preferably, the nucleic acid molecules encode polypeptides that, regardless of length, are soluble under normal physiological conditions.

The nucleic acid molecules of the invention can contain naturally occurring sequences, or sequences that differ from those that occur naturally, but, due to the degeneracy of the genetic code, encode the same polypeptide (for example, the polypeptides with SEQ ID NOS:1, 3 or 5). In addition, these nucleic acid molecules are not limited to coding sequences, e.g., they can include some or all of the non-coding sequences that lie upstream or downstream from a coding sequence.

The nucleic acid molecules of the invention can be synthesized (for example, by phosphoramidite-based synthesis) or obtained from a biological cell, such as the cell of a mammal. Thus, the nucleic acids can be those of a human, non-human primate (e.g., monkey) mouse, rat, guinea pig, cow, sheep, horse, pig, rabbit, dog, or cat.

In addition, the isolated nucleic acid molecules of the invention encompass segments that are not found as such in the natural state. Thus, the invention encompasses recombinant nucleic acid molecules (for example, isolated nucleic acid molecules encoding B7-H3 or B7-H4) incorporated into a vector (for example, a plasmid or viral vector) or into the genome of a heterologous cell or into the genome of a homologous cell at a position other than the natural chromosomal location. Recombinant nucleic acid molecules and uses therefor are discussed further below.

Certain nucleic acid molecules of the invention are antisense molecules or are transcribed into antisense molecules. These can be used, for example, to down-regulate translation of B7-H3 or B7-H4 mRNA within a cell.

Techniques associated with detection or regulation of genes are well known to skilled artisans and such techniques can be used to diagnose and/or treat disorders associated with aberrant B7-H3 or B7-H4 expression. Nucleic acid molecules of the invention are discussed further below in the context of their therapeutic utility.

A B7-H3 or B7-H4 family gene or protein can be identified based on its similarity to the relevant B7-H3 or B7-H4 gene or protein, respectively. For example, the identification can be based on sequence identity. The invention features isolated nucleic acid molecules which are at least 50% (or 55%, 65%, 75%, 85%, 95%, or 98%) identical to: (a) a nucleic acid molecule that encodes the polypeptide of SEQ ID NO:1, 3, or 5; (b) the nucleotide sequence of SEQ ID NO:2, 4, or 6; or (c) a nucleic acid molecule which includes: (i) a segment of at least 30 (e.g., at least 50, 60, 100, 125, 150, 175, 200, 225, 250, 275, 300, 325, 350, 375, 400, 425, 450, 500, 550, 600, 650, 700, 800, 900, or 940) nucleotides of SEQ ID NO:2 or SEQ ID NO:4; or (ii) a segment of at least 30 (e.g., at least 50, 60, 100, 125, 150, 175, 200, 225, 250, 275, 300, 325, 350, 375, 400, 425, 450, 500, 550, 600, 650, 700, 800, or 840 nucleotides of SEQ ID NO:6.

The determination of percent identity between two sequences is accomplished using the mathematical algorithm of Karlin and Altschul, *Proc. Natl. Acad. Sci. USA* 90, 5873-5877, 1993. Such an algorithm is incorporated into the BLASTN and BLASTP programs of Altschul et al. (1990) *J. Mol. Biol.* 215, 403-410. BLAST nucleotide searches are performed with the BLASTN program, score=100, wordlength=12 to obtain nucleotide sequences homologous to B7-H3- or B7-H4-encoding nucleic acids. BLAST protein searches are performed with the BLASTP program, score=50, wordlength=3 to obtain amino acid sequences homologous to B7-H3 or B7-H4. To obtain gapped alignments for comparative purposes, Gapped BLAST is utilized as described in Altschul et al. (1997) *Nucleic Acids Res.* 25, 3389-3402. When utilizing BLAST and Gapped BLAST programs, the default parameters of the respective programs (e.g., XBLAST and NBLAST) are used (See http://www.ncbi.nlm.nih.gov).

Hybridization can also be used as a measure of homology between two nucleic acid sequences. A B7-H3- or B7-H4-encoding nucleic acid sequence, or a portion thereof, can be used as hybridization probe according to standard hybridization techniques. The hybridization of a B7-H3 probe to DNA from a test source (e.g., a mammalian cell) is an indication of the presence of B7-H3 DNA in the test source and the hybridization of a B7-H4 probe to DNA from a test source (e.g., a mammalian cell) is an indication of the presence of B7-H4 DNA in the test source. Hybridization conditions are known to those skilled in the art and can be found in Current Protocols in Molecular Biology, John Wiley & Sons, N.Y., 6.3.1-6.3.6, 1991. Moderate hybridization conditions are defined as equivalent to hybridization in 2× sodium chloride/sodium citrate (SSC) at 30° C., followed by one or more washes in 1×SSC, 0.1% SDS at 50-60° C. Highly stringent conditions are defined as equivalent to hybridization in 6× sodium chloride/sodium citrate (SSC) at 45° C., followed by one or more washes in 0.2×SSC, 0.1% SDS at 50-65° C.

The invention also encompasses: (a) vectors that contain any of the foregoing B7-H3- and B7-H4-related coding sequences and/or their complements (that is, "antisense" sequence); (b) expression vectors that contain any of the foregoing B7-H3-related and B7-H4-related coding sequences operatively associated with any transcriptional/translational regulatory elements (examples of which are given below) necessary to direct expression of the coding sequences; (c) expression vectors containing, in addition to sequences encoding a B7-H3 or a B7-H4 polypeptide, nucleic acid sequences that are unrelated to nucleic acid sequences encoding B7-H3 or a B7-H4, such as molecules encoding a reporter, marker, or a signal peptide, e.g., fused to B7-H3 or B7-H4; and (d) genetically engineered host cells that contain any of the foregoing expression vectors and thereby express the nucleic acid molecules of the invention.

Recombinant nucleic acid molecules can contain a sequence encoding B7-H3 or B7-H4, B7-H3 having a heterologous signal sequence, or B7-H4 having an heterologous signal sequence. The full length B7-H3 polypeptide, a domain of B7-H3, or a fragment thereof may be fused to additional polypeptides, as described below. In addition, the full-length B7-H4 polypeptide, a domain of B7-H4, or a fragment thereof may be fused to additional polypeptides, as described below. Similarly, the nucleic acid molecules of the invention can encode the mature form of B7-H3 or B7-H4 or a form that includes an exogenous polypeptide which facilitates secretion.

The transcriptional/translational regulatory elements referred to above and which are further described below, include, but are not limited to, inducible and non-inducible promoters, enhancers, operators and other elements, which are known to those skilled in the art, and which drive or otherwise regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast a-mating factors.

Similarly, the nucleic acid can form part of a hybrid gene encoding additional polypeptide sequences, for example, sequences that function as a marker or reporter. Examples of marker or reporter genes include β-lactamase, chloramphenicol acetyltransferase (CAT), adenosine deaminase (ADA), aminoglycoside phosphotransferase ($nep^r$, $G418^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT). As with many of the standard procedures associated with the practice of the invention, skilled artisans will be aware of additional useful reagents, for example, additional sequences that can serve the function of a marker or reporter. Generally, the hybrid polypeptide will include a first portion and a second portion; the first portion being a B7-H3 or B7-H4 polypeptide (or a fragment of such a polypeptide) and the second portion being, for example, the reporter described above or an Ig constant region or part of an Ig constant region, e.g., the CH2 and CH3 domains of IgG2a.

The expression systems that may be used for purposes of the invention include, but are not limited to, microorganisms such as bacteria (for example, *E. coli* and *B. subtilis*) transformed with recombinant bacteriophage DNA, plasmid DNA, or cosmid DNA expression vectors containing the nucleic acid molecules of the invention; yeast (for example, *Saccharomyces* and *Pichia*) transformed with recombinant yeast expression vectors containing the nucleic acid molecules of the invention, preferably containing the nucleic acid sequence encoding B7-H3 (SEQ ID NO:2 or 4) or B7-H4 (SEQ ID NO:6); insect cell systems infected with recombinant virus expression vectors (for example, baculovirus) containing the nucleic acid molecules of the invention; plant cell systems infected with recombinant virus expression vectors (for example, cauliflower mosaic virus (CaMV) and tobacco mosaic virus (TMV)) or transformed with recombinant plasmid expression vectors (for example, Ti plasmid) containing B7-H3 or B7-H4 nucleotide sequences; or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter). Also useful as host cells are primary or secondary cells obtained directly from a mammal transfected with a plasmid vector or infected with a viral vector.

Polypeptides and Polypeptide Fragments

The polypeptides of the invention include B7-H3, B7-H4, and functional fragments of these polypeptides. The polypeptides embraced by the invention also include fusion proteins which contain either full-length B7-H3 or B7-H4 or a functional fragment of either polypeptide fused to an unrelated amino acid sequence. The unrelated sequences can be additional functional domains or signal peptides. Signal peptides are described in greater detail and exemplified below. The polypeptides can also be any of those described above but with one or more conservative substitutions.

The polypeptides can be purified from natural sources (e.g., blood, serum plasma, tissues or cells such as T cells or any cell that naturally produces B7-H3 or B7-H4). Smaller peptides (less than 50 amino acids long) can also be conveniently synthesized by standard chemical means. In addition, both polypeptides and peptides can be produced by standard in vitro recombinant DNA techniques and in vivo recombination/genetic recombination (e.g., transgenesis), using the nucleotide sequences encoding the appropriate polypeptides or peptides. Methods well known to those skilled in the art can be used to construct expression vectors containing relevant coding sequences and appropriate transcriptional/translational control signals. See, for example, the techniques described in Sambrook et al., Molecular Cloning: A Laboratory Manual (2nd Ed.) [Cold Spring Harbor Laboratory, N.Y., 1989], and Ausubel et al., Current Protocols in Molecular Biology, [Green Publishing Associates and Wiley Interscience, N.Y., 1989].

Polypeptides and fragments of the invention also include those described above, but modified for in vivo use by the addition, the amino- and/or carboxyl-terminal ends, of a blocking agent to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the peptides can be covalently or noncovalently coupled to pharmaceutically acceptable "carrier" proteins prior to administration.

Also of interest are peptidomimetic compounds that are designed based upon the amino acid sequences of the functional peptide fragments. Peptidomimetic compounds are synthetic compounds having a three-dimensional conformation (i.e., a "peptide motif") that is substantially the same as the three-dimensional conformation of a selected peptide. The peptide motif provides the peptidomimetic compound with the ability to co-stimulate T cells in a manner qualitatively identical to that of the B7-H3 or B7-H4 functional peptide fragment from which the peptidomimetic was derived. Peptidomimetic compounds can have additional characteristics that enhance their therapeutic utility, such as increased cell permeability and prolonged biological half-life.

The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

Methods of Co-stimulating a T Cell

The methods of the invention involve contacting a T cell with a B7-H3 or B7-H4 polypeptide of the invention, or a functional fragment thereof, in order to co-stimulate the T cell. Such polypeptides or functional fragments can have amino acid sequences identical to wild-type sequences or they can contain one or more conservative substitutions. The contacting can occur before, during, or after activation of the T cell. Contacting of the T cell with the B7-H3 or B7-H4 polypeptide will preferably be at substantially the same time as activation. Activation can be, for example, by exposing the T cell to an antibody that binds to the TCR or one of the polypeptides of the CD3 complex that is physically associated with the TCR. Alternatively, the T cell can be exposed to either an alloantigen (e.g., a MHC alloantigen) on, for example, an antigen presenting cell (APC) (e.g., a dendritic cell, a macrophage, a monocyte, or a B cell) or an antigenic peptide produced by processing of a protein antigen by any of the above APC and presented to the T cell by MHC molecules on the surface of the APC. The T cell can be a CD4+ T cell or a CD8+ T cell. The B7-H3 or B7-H4 polypeptide can be added to the solution containing the cells, or it can be expressed on the surface of an APC, e.g., an APC presenting an alloantigen or an antigen peptide bound to an MHC molecule. Alternatively, if the activation is in vitro, the B7-H3 or B7-H4 polypeptide can be bound to the floor of a the relevant culture vessel, e.g., a well of a plastic microtiter plate.

The methods can be performed in vitro, in vivo, or ex vivo. In vitro application of B7-H3 or B7-H4 can be useful, for example, in basic scientific studies of immune mechanisms or for production of activated T cells for use in either studies on T cell function or, for example, passive immunotherapy. Furthermore, B7-H3 or B7-H4 could be added to in vitro assays (e.g., in T cell proliferation assays) designed to test for immunity to an antigen of interest in a subject from which the T cells were obtained. Addition of B7-H3 or B7-H4 to such assays would be expected to result in a more potent, and therefore more readily detectable, in vitro response. However, the methods of the invention will preferably be in vivo or ex vivo (see below).

The B7-H3 and B7-H4 proteins and variants thereof are generally useful as immune response-stimulating therapeutics. For example, the polypeptides of the invention can be used for treatment of disease conditions characterized by immunosuppression: e.g., cancer, AIDS or AIDS-related complex, other virally or environmentally-induced conditions, and certain congenital immune deficiencies. The polypeptides may also be employed to increase immune function that has been impaired by the use of radiotherapy of immunosuppressive drugs such as certain chemotherapeutic agents, and therefore are particularly useful when given in conjunction with such drugs or radiotherapy. The polypeptides can, furthermore, be used to enhance immune responses in normal subjects.

These methods of the invention can be applied to a wide range of species, e.g., humans, non-human primates, horses, cattle, pigs, sheep, goats, dogs, cats, rabbits, guinea pigs, hamsters, rats, and mice.

In Vivo Approaches

In one in vivo approach, a B7-H3 or B7-H4 polypeptide (or a functional fragment thereof) itself is administered to the subject. Generally, the compounds of the invention will be suspended in a pharmaceutically-acceptable carrier (e.g., physiological saline) and administered orally or by intravenous infusion, or injected subcutaneously, intramuscularly, intraperitoneally, intrarectally, intravaginally, intranasally, intragastrically, intratracheally, or intrapulmonarily. They are preferably delivered directly to an appropriate lymphoid tissue (e.g. spleen, lymph node, or mucosal-associated lymphoid tissue (MALT)). The dosage required depends on the choice of the route of administration, the nature of the formulation, the nature of the patient's illness, the subject's size, weight, surface area, age, and sex, other drugs being administered, and the judgment of the attending physician. Suitable dosages are in the range of 0.01-100.0 µg/kg. Wide variations in the needed dosage are to be expected in view of the variety of polypeptides and fragments available and the differing efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2- or 3-, 4-, 6-, 8-, 10-, 20-, 50-, 100-, 150-, or more fold). Encapsulation of the polypeptide in a suitable delivery vehicle (e.g., polymeric microparticles or implantable devices) may increase the efficiency of delivery, particularly for oral delivery.

Alternatively, a polynucleotide containing a nucleic acid sequence encoding the B7-H3 or B7-H4 polypeptide or functional fragment thereof can be delivered to an appropriate cell of the animal. Expression of the coding sequence will preferably be directed to lymphoid tissue of the subject by for example, delivery of the polynucleotide to the lymphoid tissue. This can be achieved by, for example, the use of a polymeric, biodegradable microparticle or microcapsule delivery vehicle, sized to optimize phagocytosis by phagocytic cells such as macrophages. For example, PLGA (poly-lacto-co-glycolide) microparticles approximately 1-10 µm in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis i.e., larger than 5 µm and preferably larger than 20 µm.

Another way to achieve uptake of the nucleic acid is using liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells [Cristiano et al. (1995), *J. Mol. Med.* 73, 479]. Alternatively, lymphoid tissue specific targeting can be achieved by the use of lymphoid tissue-specific transcriptional regulatory elements (TRE) such as a B lymphocyte, T lymphocyte, or dendritic cell specific TRE. Lymphoid tissue specific TRE are known [Thompson et al. (1992), *Mol. Cell. Biol.* 12, 1043-1053; Todd et al. (1993), *J. Exp. Med.* 177, 1663-1674; Penix et al. (1993), *J. Exp. Med.* 178, 1483-1496]. Delivery of "naked DNA" (i.e., without a delivery vehicle) to an intramuscular, intradermal, or subcutaneous site, is another means to achieve in vivo expression.

In the relevant polynucleotides (e.g., expression vectors) the nucleic acid sequence encoding the B7-H3 or B7-H4 polypeptide or functional fragment of interest with an initiator methionine and optionally a targeting sequence is operatively linked to a promoter or enhancer-promoter combination.

Short amino acid sequences can act as signals to direct proteins to specific intracellular compartments. For example, hydrophobic signal peptides (e.g., MAISGVPVLGFFIIAV-LMSAQESWA (SEQ ID NO:7)) are found at the amino terminus of proteins destined for the ER. While the sequence KFERQ (SEQ ID NO:8) (and other closely related sequences) is known to target intracellular polypeptides to lysosomes, other sequences (e.g., MDDQRDLISNNEQLP (SEQ ID NO:9) direct polypeptides to endosomes. In addition, the peptide sequence KDEL (SEQ ID NO:10) has been shown to act as a retention signal for the ER. Each of these signal peptides, or a combination thereof, can be used to traffic the B7-H3 or B7-H4 polypeptides or functional fragments of the invention as desired. DNAs encoding the B7-H3 or B7-H4 polypeptides or functional fragments containing targeting signals will be generated by PCR or other standard genetic engineering or synthetic techniques.

A promoter is a TRE composed of a region of a DNA molecule, typically within 100 basepairs upstream of the point at which transcription starts. Enhancers provide expression specificity in terms of time, location, and level. Unlike a promoter, an enhancer can function when located at variable distances from the transcription site, provided a promoter is present. An enhancer can also be located downstream of the transcription initiation site. To bring a coding sequence under the control of a promoter, it is necessary to position the translation initiation site of the translational reading frame of the peptide or polypeptide between one and about fifty nucleotides downstream (3') of the promoter. The coding sequence of the expression vector is operatively linked to a transcription terminating region.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles which are suitable for administration to a human, e.g., physiological saline. A therapeutically effective amount is an amount of the polynucleotide which is capable of producing a medically desirable result (e.g., an enhanced T cell response) in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to $10^{12}$ copies of the polynucleotide molecule. This dose can be repeatedly administered, as needed. Routes of administration can be any of those listed above.

Included in these in vivo approaches, are methods of co-stimulating a T cell that involve administering more than ene co-stimulatory molecule or functional fragment thereof. Such combinations can be any combination of one or more of co-stimulatory polypeptides, e.g., B7-1, B7-2, B7-H1, B7-H2, B7-H3, B7-H4, 4-1BB, OX40, or HVEM and functional fragments of any of these. The proteins or functional fragments per se can be administered (as above) or nucleic acids (e.g., expression vectors) encoding the proteins or functional fragments can be administered (as above). Where expression vectors are used, a single vector containing coding sequences for two or more of the co-stimulatory polypeptides or functional fragments can be administered. Alternatively, multiple (e.g., 2, 3, 4, 5, or 6) individual vectors, each encoding one or more (e.g., 2, 3, 4, 5, or 6) of the co-stimulatory polypeptides or functional fragments thereof can be administered.

Ex Vivo Approaches

Peripheral blood mononuclear cells (PBMC) can be withdrawn from the patient or a suitable donor and exposed ex vivo to an activating stimulus (see above) and a B7-H3 or B7-H4 polypeptide or polypeptide fragment (whether in soluble form or attached to a sold support by standard methodologies). The PBMC containing highly activated T cells are then introduced into the same or a different patient.

An alternative ex vivo strategy can involve transfecting or transducing cells obtained from the subject with a polynucleotide encoding a B7-H3 or B7-H4 polypeptide or functional fragment-encoding nucleic acid sequences described above. The transfected or transduced cells are then returned to the subject. While such cells would preferably be hemopoietic cells (e.g., bone marrow cells, macrophages, monocytes, dendritic cells, or B cells) they could also be any of a wide range of types including, without limitation, fibroblasts, epithelial cells, endothelial cells, keratinocytes, or muscle cells in which they act as a source of the B7-H3 or B7-H4 polypeptide or functional fragments thereof for as long as they survive in the subject. The use of hemopoietic cells, that include the above APC, would be particularly advantageous in that such cells would be expected to home to, among others, lymphoid tissue (e.g., lymph nodes or spleen) and thus the B7-H3 or B7-H4 polypeptide or functional fragment would be produced in high concentration at the site where they exert their effect, i.e., enhancement of an immune response. In addition, if APC are used, the APC expressing the exogenous B7-H3 or B7-H4 molecule can be the same APC that presents an alloantigen or antigenic peptide to the relevant T cell. The B7-H3 or B7-H4 polypeptides can be secreted by the APC or expressed on its surface. Prior to returning the recombinant APC to the patient, they can optionally be exposed to sources of antigens or antigenic peptides of interest, e.g., those of tumors, infectious microorganisms, or autoantigens. The same genetic constructs and trafficking sequences described for the in vivo approach can be used for this ex vivo strategy. Furthermore, tumor cells, preferably obtained from a patient, can be transfected or transformed by a vector encoding a B7-H3 or B7-H4 polypeptide or functional fragment thereof. The tumor cells, preferably treated with an agent (e.g., ionizing irradiation) that ablates their proliferative capacity, are then returned to the patient where, due to their expression of the exogenous B7-H3 or B7-H4 (on their cell surface or by secretion), they can stimulate enhanced tumoricidal T cell immune responses. It is understood that the tumor cells which, after transfection or transformation, are injected into the patient, can also have been originally obtained from an individual other than the patient.

The ex vivo methods include the steps of harvesting cells from a subject, culturing the cells, transducing them with an expression vector, and maintaining the cells under conditions suitable for expression of the B7-H3 or B7-H4 polypeptide or functional fragment. These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced are then selected, for example, for expression of the coding sequence or of a drug resistance gene. The cells may then be lethally irradiated (if desired) and injected or implanted into the patient.

It is understood that in these ex vivo procedures, the cells to be introduced into a subject can be transfected or transformed with one or more (e.g., two, three, four, five, or six) expression vectors containing one or more (e.g., two, three, four, five, or six) sequences encoding any of the co-stimulatory molecules listed above (e.g., B7-1, B7-2, B7-H1, B7-H2, B7-H3, or B7-H4) or functional fragments thereof prior to introduction.
Methods of Screening for Compounds that Inhibit or Enhance Immune Responses.

The invention provides methods for testing compounds (small molecules or macromolecules) that inhibit or enhance an immune response. Such a method can involve, e.g., culturing a B7-H3 or B7-H4 polypeptide of the invention (or a functional fragment thereof) with T cells in the presence of a T cell stimulus (see above). The B7-H3 or B7-H4 molecule can be in solution or membrane bound (e.g., expressed on the surface of the T cells) and it can be natural or recombinant. Furthermore, the B7-H3 or B7-H4 polypeptides (or functional fragments thereof) can have amino acid sequences identical to wild-type sequences or they can have one or more conservative substitutions. Compounds that inhibit the T cell response will likely be compounds that inhibit an immune response while those that enhance the T cell response will likely be compounds that enhance an immune response.

The invention also relates to using B7-H3 or B7-H4 or functional fragments thereof to screen for immunomodulatory compounds that can interact with B7-H3 or B7-H4. One of skill in the art would know how to use standard molecular modeling or other techniques to identify small molecules that would bind to T cell interactive sites of B7-H3 or B7-H4. One such example is provided in Broughton (1997) Curr. Opin. Chem. Biol. I, 392-398.

A candidate compound whose presence requires at least 1.5-fold (e.g., 2-fold, 4-fold, 6-fold, 10-fold, 150-fold, 1000-fold, 10,000-fold, or 100,000-fold) more B7-H3 or B7-H4 in order to achieve a defined arbitrary level of T cell activation than in the absence of the compound can be useful for inhibiting an immune response. On the other hand, a candidate compound whose presence requires at least 1.5 fold (e.g., 2-fold, 4-fold, 6-fold, 10-fold, 100-fold, 1000-fold, 10,000 fold, or 100,000-fold) less B7-H3 or B7-H4 to achieve a defined arbitrary level of T cell activation than in the absence of the compound can be useful for enhancing an immune response. Compounds capable of interfering with or modulating B7-H3 or B7-H4 function are good candidates for immunosuppressive immunoregulatory agents, e.g., to modulate an autoimmune response or suppress allogeneic or xenogeneic graft rejection.
B7-H3 and B7-H4 Antibodies The invention features antibodies that bind to the B7-H3 or B7-H4 polypeptides or fragments of such polypeptides. Such antibodies can be polyclonal antibodies present in the serum or plasma of animals (e.g., mice, rabbits, rats, guinea pigs, sheep, horses, goats, cows, or pigs) which have been immunized with the relevant B7-H3 or B7-H4 polypeptide or peptide fragment using methods, and optionally adjuvants, known in the art. Such polyclonal antibodies can be isolated from serum or plasma by methods known in the art. Monoclonal antibodies that bind to the above polypeptides or fragments are also embodied by the invention. Methods of making and screening monoclonal antibodies are well known in the art.

Once the desired antibody-producing hybridoma has been selected and cloned, the resultant antibody can be produced in a number of methods known in the art. For example, the hybridoma can be cultured in vitro in a suitable medium for a suitable length of time, followed by the recovery of the desired antibody from the supernatant. The length of time and medium are known or can be readily determined.

Additionally, recombinant antibodies specific for B7-H3 or B7-H4, such as chimeric and humanized monoclonal antibodies comprising both human and non-human portions, are within the scope of the invention. Such chimeric and humanized monoclonal antibodies can be produced by recombinant DNA techniques known in the art, for example, using methods described in Robinson et al., International Patent Publication PCT/US86/02269; Akira et al., European Patent Application 184,187; Taniguchi, European Patent Application 171, 496; Morrison et al., European Patent Application 173,494; Neuberger et al., PCT Application WO 86/01533; Cabilly et al., U.S. Pat. No. 4,816,567; Cabilly et al., European Patent Application 125,023; Better et al. (1988) Science 240, 1041-43; Liu et al. (1987) J. Immunol. 139, 3521-26; Sun et al. (1987) PNAS 84, 214-18; Nishimura et al. (1987) Canc. Res. 47, 999-1005; Wood et al. (1985) Nature 314, 446-49; Shaw et al. (1988) J. Natl. Cancer Inst. 80, 1553-59; Morrison, (1985) Science 229, 1202-07; Oi et al. (1986) BioTechniques 4, 214; Winter, U.S. Pat. No. 5,225,539; Jones et al. (1986) Nature 321, 552-25; Veroeyan et al. (1988) Science 239, 1534; and Beidler et al. (1988) J. Immunol. 141, 4053-60.

Also included within the scope of the invention are antibody fragments and derivatives which contain at least the functional portion of the antigen binding domain of an antibody that binds specifically to B7-H3 or B7-H4. Antibody fragments that contain the binding domain of the molecule can be generated by known techniques. For example, such fragments include, but are not limited to: $F(ab')_2$ fragments which can be produced by pepsin digestion of antibody molecules; Fab fragments which can be generated by reducing the disulfide bridges of $F(ab')_2$ fragments; and Fab fragments which can be generated by treating antibody molecules with papain and a reducing agent. See, e.g., National Institutes of Health, 1 Current Protocols In Immunology, Coligan et al., ed. 2.8, 2.10 (Wiley Interscience, 1991). Antibody fragments also include Fv (e.g., single chain Fv (scFv)) fragments, i.e., antibody products in which there are no constant region amino acid residues. Such fragments can be produced, for example, as described in U.S. Pat. No. 4,642,334 which is incorporated herein by reference in its entirety.

The following examples are meant to illustrate, not limit, the invention.

EXAMPLE 1

Materials and Methods

Cell Lines, Cell Preparation and Activation. The adenovirus-transformed human kidney epithelial line 293 and the histocytic lymphoma line U937 were purchased from ATCC (Manassas, Va.). The 624me1 melanoma line was a gift from Dr. Rang-Fu Wang (Surgery Branch, NCI). Cell lines were grown and maintained in DMEM or RPMI 1640 media (GIBCO, Gaithersburg, Md.) supplemented with 10% fetal bovine serum (FBS) (HyClone, Logan, Utah), 25 mM HEPES (Life Technologies, Grand Island, USA), 2 mM L-glutamine (Life Technologies), 100 U/ml penicillin (Life Technologies), 100 µg/ml streptomycin (Life Technologies), and $5 \times 10^{-5}$ M 2-mercaptoethanol (V WR, Chicago, Ill.). Methods for the preparation of peripheral blood mononuclear cells (PBMC) from healthy donors and monocyte-derived dendritic cells (DC) were described previously [Chapoval et al. (2000) *Blood*. 95, 2346-2351]. Fluorescence flow cytometry (FFC) analysis using monoclonal antibodies (mAb) specific for B7-1, B7-2, and MHC class II indicated that >99% of cells in the monocyte-derived DC preparations had a typical DC phenotype. Total T cell-enriched populations were obtained by passing nonadherent PBMC through nylon wool columns as described previously [Tamada et al. (2000) *J. Immunol.* 164, 4105-4110]. CD4$^+$ and CD8$^+$ T cell subsets were further purified using the MACS magnetic bead system (Miltenyl Biotec, Auburn, Calif.) according to the manufacturer's instructions. The purity of the T cell subset preparations were >98% based on FFC analysis using T cell subset-specific mAb. For the activation of U937 cells or DC, the cells ($1\times10^6$ cells/ml) were cultured for 24 h with lipopolysaccharide (LPS; 1 µg/ml). Adherent PBMC were activated with a combination of LPS (100 ng/ml) and human interferon-γ (IFN-γ; 1500 IU/ml; R&D Systems, Minneapolis Minn.). For activation of T and B cells, PBMC ($2.5\times10^6$ cells/ml) were cultured for 24 h with phytohemagglutinin (PHA; (5 µg/ml)) or LPS (1 µg/ml), respectively. All cell types were also activated with phorbol myristic acid (PMA; 5 ng/ml) and ionomycin (250 ng/ml).

Cloning and Sequencing of Full-Length Human B7-H3 cDNA. The National Center for Biotechnology Information (NCBI) and Human Genome Sciences, Inc. expressed sequence tag (EST) databases containing the sequences of >500 different cDNA libraries were screened for cDNA sequences having homology to published B7-1, B7-2, B7-H1, and B7-H2 sequences using the BLASTN and TBLASTN algorithms. Information obtained from this screening was used to generate appropriate PCR primers and full-length human cDNA molecules encoding B7-H3 was generated by PCR from a THP-1 cDNA library prepared by the SMART PCR cDNA synthesis kit (Clontech, Palo Alto, Calif.). The resulting PCR product was cloned into the pcDNA3.1(−) vector (Invitrogen, Carlsbad, Calif.). The nucleotide sequence of the B7-H3 encoding cDNA molecules was verified by sequencing of several independent clones. For transient expression of the B7-H3 gene, the vector containing full-length B7-H3.1 encoding cDNA (pcDNA/B7-H3) or control parental vector (pcDNA3.1(−)) was transfected into 293 or 624mel cells by Fugene 6 (Boeheringer-Mannheim) according to the manufacturer's instructions.

Production of Fusion Proteins. Recombinant B7-H3Ig fusion protein was prepared by fusing the coding region of the extracellular domain of B7-H3 to the Fc constant region of mouse IgG2a as described previously [Chapoval et al. (2000). Methods Mol. Med. 45.247-255]. An expression vector containing a DNA sequence encoding B7-H3Ig was transfected into 293 cells by calcium phosphate precipitation and cultured in serum-free DMEM. The supernatant was collected at 72 h and the fusion protein was purified by Protein G sepharose columns (Pharmacia, Uppsala, Sweden). The purity and expected molecular weight of the fusion protein were confirmed by electrophoresis on polyacrylamide gels and by Western blot using the anti-B7-H3 antibody described below. Analogous fusion proteins (ICOSIg, B7-1Ig, and CTLA4Ig) containing the extracellular domains of ICOS, B7-1, and CTLA4, respectively, were prepared by a similar method.

RNA Analysis. The expression of B7-H3 mRNA in human tissues was analyzed using human multiple-tissue and tumor line Northern blots purchased from Clontech (Palo Alto, Calif.). Full-length cDNA encoding B7-H3 was labeled with [$^{32}$P]-dCTP and hybridized to filter membranes according to the manufacturer's protocol.

Immunization, Antibody Production and FACS Analysis. For production of antibody specific for human B7-H3, a peptide consisting of amino acids 142-165 (YSKPSMTLEP-NKDLRPGDTVTITC) (SEQ ID NO:12) spanning a hydrophilic region of B7-H3 was synthesized and conjugated to KLH as described previously [Tamada et al. (2000) *J. Immunol.* 164, 4105-4110]. Polyclonal antibodies were prepared by immunizing BALB/c mice with the peptide in complete Freund's adjuvant (Sigma) and subsequently boosting two times with the peptides in incomplete Freund's adjuvant. Blood was collected and sera prepared 10 days after the final boost. The specificity of the antiserum was determined by ELISA against B7-H3Ig and indirect immunofluorescence of 293 cells transfected to express B7-H3, B7-H2, B7-H1, and B7-1. Serum prepared from the blood of non-immunized BALB/c mice was used as a negative control. Substantially identical results were obtained with two antisera generated in the same way by immunization of mice with B7-H3 hydrophilic region peptides corresponding to amino acid residues 166-189 (SSYRGYPEAEVFWQDGQGVPLTGN) (SEQ ID NO:13) of B7-H3.1 or amino acid residues 223-247 (RNPV-LQQDAHGSVTITGQPMTFPPE) (SEQ ID NO:14) of B7-H3.

For analysis of B7-H3 expression and B7-H3 interaction with a putative counter-receptor, cells were incubated either with anti-B7-H3 antibodies (1:1000 dilution in PBS), CTLA4Ig (5 µg/sample) or ICOSIg (5 µg/sample) on ice. After a 45 min incubation, cells were washed and cultured for 45 min with fluorescein isothiocyanate (FITC)-conjugated goat anti-mouse Ig F(ab')$_2$ (BioSource, Camarillo, Calif.). For two color staining, cells were washed and further incubated with phycoerythrin (PE)-conjugated mAb specific for CD3, CD14, or CD19 (PharMingen, San Diego, Calif.). For the analysis of CD3+, CD19+, and CD14+ cells, peripheral blood mononuclear cells (PBMC) (untreated or activated as described below) were stained with anti-B3-H7 antiserum (green fluorescence) and either anti-CD3, anti-CD19, or anti-CD14 monoclonal antibody (mAb) (orange fluorescence). The proportion of B7-H3 expressing cells (green fluorescence) within the CD3+, the CD19+, and the CD14+ populations was assessed by gating the flow cytometer on the relevant populations (orange fluorescence). Expression of a B7-H3 counter-receptor was analyzed by incubation of cells with B7-H3Ig (5 µg/sample) with subsequent staining using FITC-conjugated goat anti-mouse Ig F(ab')$_2$. Single or double stained cells were analyzed using the Becton Dickinson FACScan (Mountain View, Calif.).

T cell proliferation an cytokine and cytokine production assay. T cell proliferation was measured as previously described [Dong et al. (1999) *Nat. Med.* 5, 1365-1369]. Briefly, flat-bottom 96-well microtiter culture plates were coated at 4° C. overnight with 50 µl/well of anti-CD3 mAb (40 ng/ml) and subsequently coated with the indicated concentrations of B7-H3Ig, B7-1Ig, or control Ig at 37° C. for 4 h. T cells were added to the wells at the indicated concentrations. For measurement of T cell proliferation, the plates were cultured for 72 h and [$^3$H]-thymidine (1 µCi/well) was added 18 h prior to harvesting of the cultures. [$^3$H]-thymidine incorporation was measured with a MicroBeta Trilix liquid scintillation counter (Wallac, Turku, Finland). For measurements of cytokine (interleukin- (IL-)2, IL-10, and interferon-γ (IFN-γ) production, supernatants were removed from the cultures at the indicated times after culture initiation and subjected to ELISA for the cytokines using commercially available ELISA kits (PharMingen).

CTL generation and cytotoxicity assay. CTL were generated in 24-well culture plates by co-culturing of nylon wool column-purified T cells ($5\times10^6$ cells/well) in the presence of irradiated (10,000 rad) 624me1 cells ($1\times10^5$ cells/well) transfected with either pcDNA/B7-H3 or control parent pcDNA3.1(−) plasmid. The cultured cells were harvested on day 5 and CTL activity against parental 624me1 was measured in a standard 4 h $^{51}$Cr-release assay [Chapoval et al. (1998) *J. Immunol.* 161, 6977-6984].

Cytokine gene expression. Total RNA was prepared using TRI Reagent (Sigma) from $5\times10^6$ T cells which had been cultured in 24-well tissue culture plates for 72 h with a sub-optimal dose of anti-CD3 antibody (coated onto tissue culture plate wells at a concentration of 200 ng/ml) and with either control Ig (coated onto tissue culture plate wells at a concentration of 5 µg/ml), B7-1Ig (coated onto tissue culture plate wells at a concentration of 5 ug/ml), or B7-H3Ig (coated onto tissue culture plate wells at a concentration of 5 ug/ml). Ten micrograms of the total RNA from each of the three cell populations were used as a template to produce $^{32}$P labeled cDNA by standard procedures using retroviral (MMTV) reverse transcriptase (Promega, Madison, Wis.) and [$\alpha$-$^{32}$P]-dCTP (NEN, Boston, Mass.). The Human Common Cytokine-1 GEArray Kit (No hGEA9912099, SuperArray Inc. Bethesda, Md.) was used to determine the relative amounts of cDNA encoding 23 different cytokines (see FIG. 14) in the three $^{32}$P labeled cDNA samples as an indirect measure of the of the relative amounts of corresponding mRNA in the three cell populations. The kit includes cytokine mRNA arrays which are membranes containing mRNA encoding the 23 cytokines and two house keeping protein, beta-actin and glyceraldehyde-3-phosphate dehydrogenase (GAPDH) bound to discrete areas of the membrane. A separate array was exposed under standard hybridization conditions to each of the three $^{32}$P labeled cDNA samples and the three arrays were washed under washing conditions specified by the manufacturer. A STORM Phosphoimager system (Molecular Dynamics, Sunnyvale, Calif.) was used to measure the signals due to hybridization of $^{32}$P labeled cDNA to appropriate areas on the membranes. The data are expressed as arbitrary units calculated by the following formula:

Arbitrary units=(Cytokine signal−background signal)/ (beta-actin signal−background signal)

EXAMPLE 2

Molecular Cloning and Expression Pattern of B7-H3-encoding DNA

Figure 5A:
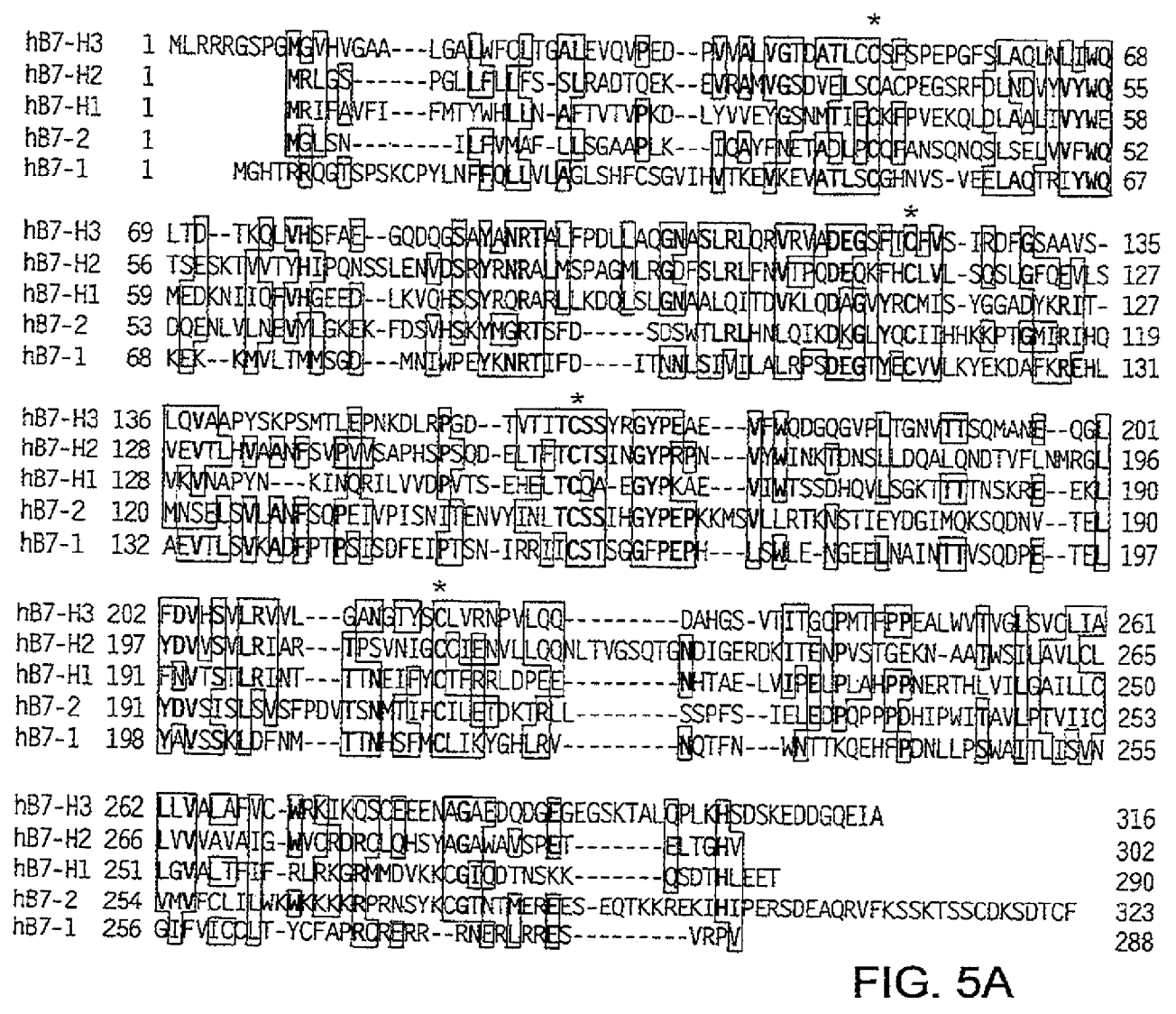

The EST databases of NCBI and Human Genome Sciences, Inc. were screened for sequences homologous to the DNA sequences encoding the extracellular regions of all published B7 family members. By a PCR-based strategy using primers based on EST sequences of interest, two open reading frames (orf) encoding two different allelic forms of a B7-like molecule were identified in a human dendritic cell (DC)-derived cDNA library. The nucleic acid sequences were confirmed by analyses of independent RT-PCR products from human THP-1 and DC library. The two sequences, which differed by a single nucleotide and most likely corresponding to B7-H3 alleles, were observed by sequencing several independent clones obtained from several independent PCRs. In one allele (SEQ ID NO:2) (B7H-3.1) nucleotide 496 is a T (FIG. 1) and in the second allele (B7H-3.2) (SEQ ID NO:4) nucleotide 496 is a C (FIG. 2). At the protein level, B7-H3.1 (SEQ ID NO:1) contains a serine residue at position 166 (FIG. 3) and B7-H3.2 (SEQ ID NO: 2) contains a proline residue at position 166 (FIG. 4). Except at position 166, B7-H3.1 and B7-H3.2 have identical amino acid sequences. The B7-H3.1 orf encodes a putative 316 amino acid protein (B7-H3) that shares identity in its predicted extracellular receptor-binding domain with human B7-H1 (27%), B7-H2 (25%), B7-1 (21%), and B7-2 (20%) (FIG. 5A). The putative B7-H3 protein contains a typical signal peptide in its N-terminus, a single extracellular V-like Ig domain and a single C-like Ig domains, a transmembrane region, and a 45 amino acid cytoplasmic tail (FIG. 5B), indicating that B7-H3 is a type I transmembrane protein belonging to the Ig superfamily. Similar to other members of the family, B7-H3 has four conserved cysteine residues that are believed to be involved in the formation of V- and C-like Ig domains. The absence of a heptad structure and B30.2 domains makes B7-H3 distinct from butyrophilins and myelin oligodendrocyte glycoproteins [reviewed in Linsley, et al. (1994) *Protein Sci.* 3, 1341-1343; Henry et al. (1999) *Immunol. Today* 20, 285-288]. The above data indicate that B7-H3 is a member of the B7 costimulatory ligand family.

Northern blot analysis indicated that B7-H3 is encoded by a single 4.1-kb mRNA and is expressed at high levels in many normal human tissues including heart, liver, placenta, prostate, testis, uterus, pancreas, small intestine, and colon; low levels of B7-H3 mRNA were also found in brain, skeletal muscle, kidney, and lung. B7-H3 mRNA could also be detected in several lymphoid organs including spleen, lymph nodes, bone marrow, fetal liver, and thymus. Surprisingly, no B7-H3 mRNA was detected in RNA from PBMC in two independent northern blots. Several tumor lines, including melanoma G361, cervix adenocarcinoma HeLa S3, chronic myelogenous leukemia K562, lung carcinoma A546, and colorectal adenocarcinoma SW480, also express B7-H3 mRNA. Molt-4 (lymphoblastic leukemia) and Raji (Burkitts lymphoma) were negative for B7-H3 mRNA. Equal levels of actin mRNA were observed in all the blots. Using RT-PCR, B7-H3 mRNA was detectable in RNA from K562, U937, THP-1, and dendritic cells but not in Raji, Jurkat, Molt-4, or a T cell clone.

Figure 6B:
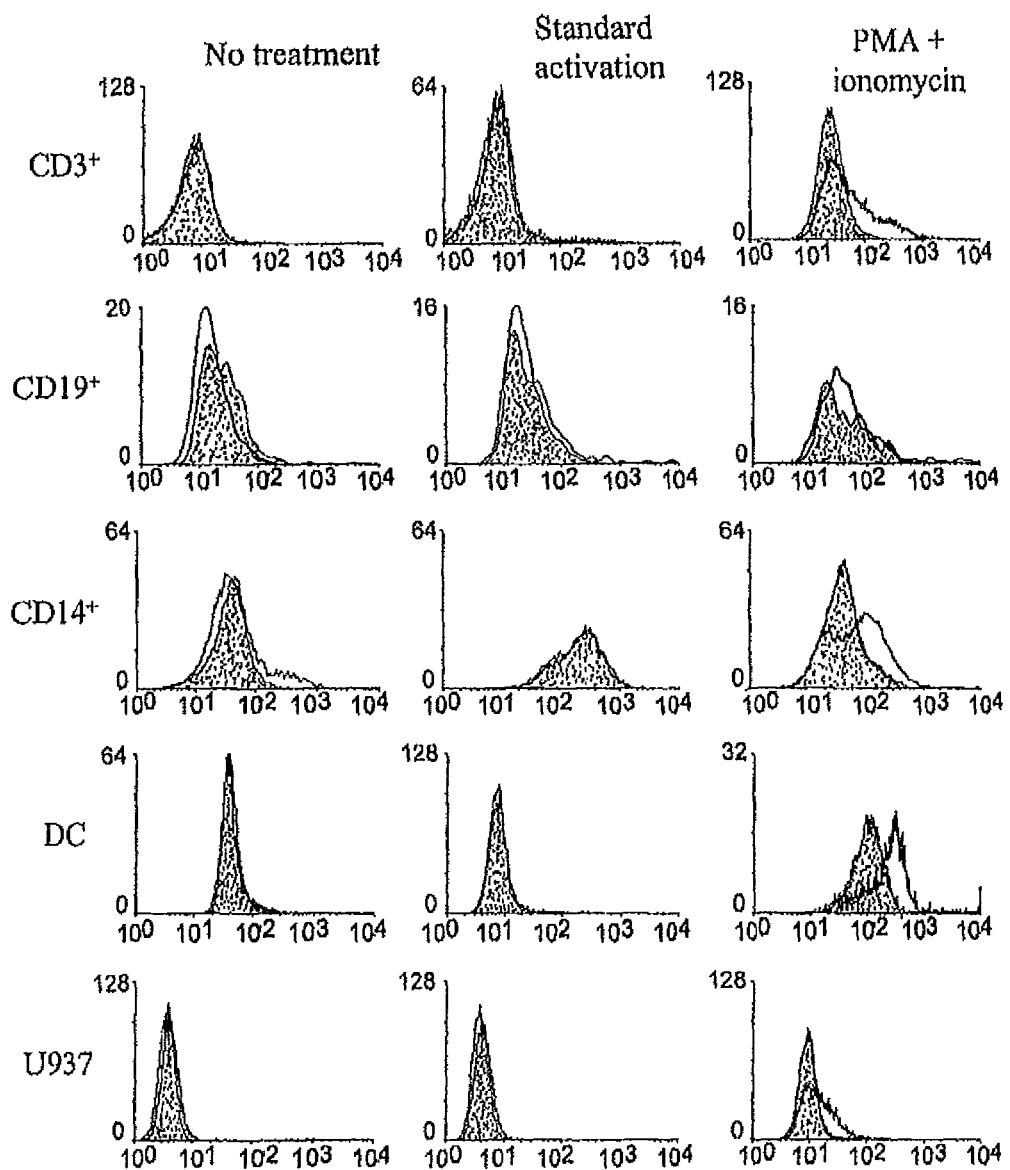
FIG. 6B is a series of fluorescence flow cytometry histograms showing the staining by an anti-B7-H3 antiserum (open area) or control serum (shaded area) of various cell types.

FFC analysis was performed to detect cell-surface expression of B7-H3 protein. Polyclonal antibodies specific for human B7-H3 were generated by immunizing mice with KLH-conjugated synthetic peptides spanning the hydrophilic regions of human B7-H3. Results obtained using an antiserum generated by immunization with a peptide containing amino acid residues 142-165 are described. The antiserum stained 293 cells transiently transfected to express B7-H3, but not B7-H1, B7-H2, nor B7-1 (FIG. 6A, 7B and data not shown), indicating that this antiserum is specific for B7-H3 protein. B7-H3 is detectable on a small fraction of resting CD14$^+$ cells (<3%), but not on resting CD3$^+$ and CD19$^+$ cells (FIG. 6B). Activation ("standard activation") of PBMC by various methods including PHA, LPS, or a combination of LPS and IFN-$\gamma$ did not modulate B7-H3 expression. In contrast, stimulation with a combination of PMA and ionomycin significantly increased surface expression of B7-H3 on CD3$^+$ and CD14$^+$ cells but not on CD19$^+$ cells (FIG. 6B). Interestingly, treatment by PMA and ionomycin (but not by LPS) also increased the expression of B7-H3 on cytokine-induced DC and on cells of the human monocytic tumor line U937 (FIG. 6B). The epithelium-derived tumor lines including choriocarcinoma BeWo, colorectal adenocarcinomas HT29, WiDr, and SW620 negative for B7-H3, with or without activation by PMA and ionomycin (data not shown). These data indicate that surface B7-H3 is not constitutively expressed on the majority of hematopoietic cells but is selectively induced by PMA and ionomycin in T cells, monocytes, and DC.

EXAMPLE 3

Expression of a B7-H3Counter-Receptor

Figure 7A:
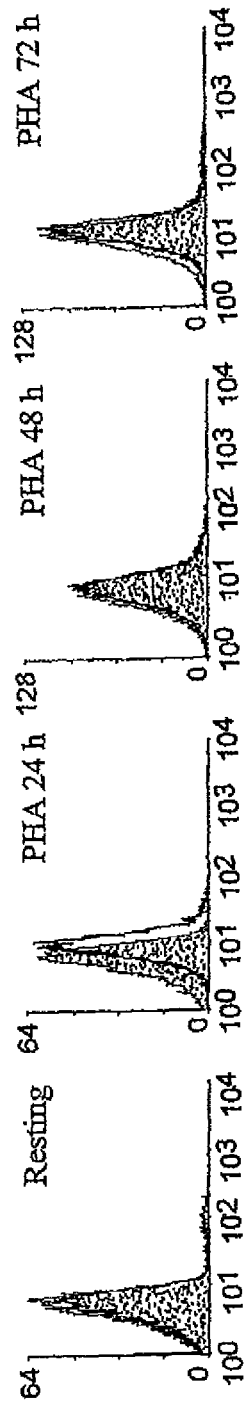
FIG. 7A is a series of fluorescence flow cytometry histograms showing the ability of B7-H3Ig fusion protein to bind to activated T cells but not to resting T cells. Unactivated nylon wool-purified T cells and nylon wool-purified T cells activated with PHA (5 µg/ml) for 24 h, 48 h, or 72 h were stained with B7-H3Ig (5 µg; open areas) or control Ig (5 µg) prior to analysis.

To determine whether a counter-receptor (B7-H3CR) for B7-H3 is expressed on T cells, a B7-H3Ig fusion protein was prepared by fusing the extracellular domain of B7-H3 and the Fc portion of mouse IgG2a. FFC analysis (FIG. 7A) indicated that purified resting T cells do not express a B7-H3CR. Stimulation of T cells with PHA, however, led to a rapid up-regulation of B7-H3CR within the first 24 h of culture. The expression waned after 48 h (FIG. 7A).

Figure 7B:
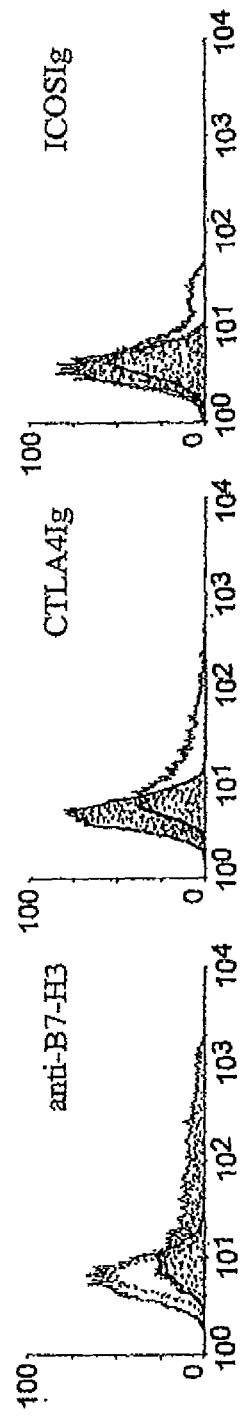
FIG. 7B is a series of fluorescence flow cytometry histograms showing the ability of anti-B7-H3 antiserum, CTLA4Ig fusion protein, and ICOSIg fusion protein to bind to 293 cells transfected with expression vectors containing either a B7-H3.1 (solid line, shaded area), B7-1 (solid line, open area), or B7-H2 (dotted line, open area) coding sequence.

293 cells were transiently transfected with pcDNA/B7-H3, stained with CTLA4Ig and ICOSIg, and subjected to FACS analysis. The cells were also stained with anti-B7-H3 antibodies as a positive control. Neither CTLA4Ig nor ICOSIg stained B7-H3/293 cells (FIG. 7B). Furthermore, while anti-B7-H3 antibodies did not bind to B7-1/293 or B7-H2/293, CTLA4Ig bound to B7-1/293 and ICOSIg bound to B7-H2/293 (FIG. 7B). Thus B7-H3 is a ligand for an inducible T cell counter-receptor distinct from CTLA-4 and ICOS.

EXAMPLE 4

B7-H3Co-stimulates T Cell Proliferation and the Generation of CTL

A previously described co-stimulation assay was used [Dong et al. (1999) *Nat. Med.* 5, 1365-1369] to test whether B7-H3 co-stimulates the proliferation of T cells. In this assay, purified T cells were stimulated by immobilized anti-CD3 mAb in the presence of immobilized B7-H3Ig. The proliferation of T cells was determined by [$^3$H]-thymidine-incorporation after a 72 h incubation. B7-H3Ig increased T cell proliferation in a dose-dependent fashion (FIG. 8A) in the presence of a suboptimal dose of anti-CD3 mAb (coated onto the plates at a concentration of 40 ng/ml). Interestingly, B7-1Ig coated onto the plates at concentrations of 2.5-10 µg/ml induced significantly higher levels of T cell proliferation than did B7-H3Ig (FIG. 8A). In the absence of anti-CD3 mAb, neither B7-H3Ig nor B7-1Ig induced proliferation of T cells. Immobilized B7-H3Ig significantly enhanced proliferation of both CD4$^+$ and CD8$^+$ T cells (FIG. 8B).

To evaluate the ability of B7-H3 to affect CTL generation, purified human T cells from healthy donors were stimulated with cells of the melanoma line 624me1 transiently transfected with pcDNAJB7-H3 or control vector. CTL activity was determined by lysis of $^{51}$Cr-labeled 624me1 cells. B7-H3/624me1 cells induced significantly higher CTL activity than did mock-transfected 624me1 cells (FIG. 8C). Thus B7-H3 co-stimulates the growth of both CD4+ and CD8+ T cells and enhances the generation of CTL.

EXAMPLE 5

Molecular Cloning and Expression Pattern of B7-H4 Encoding DNA

Figure 11:
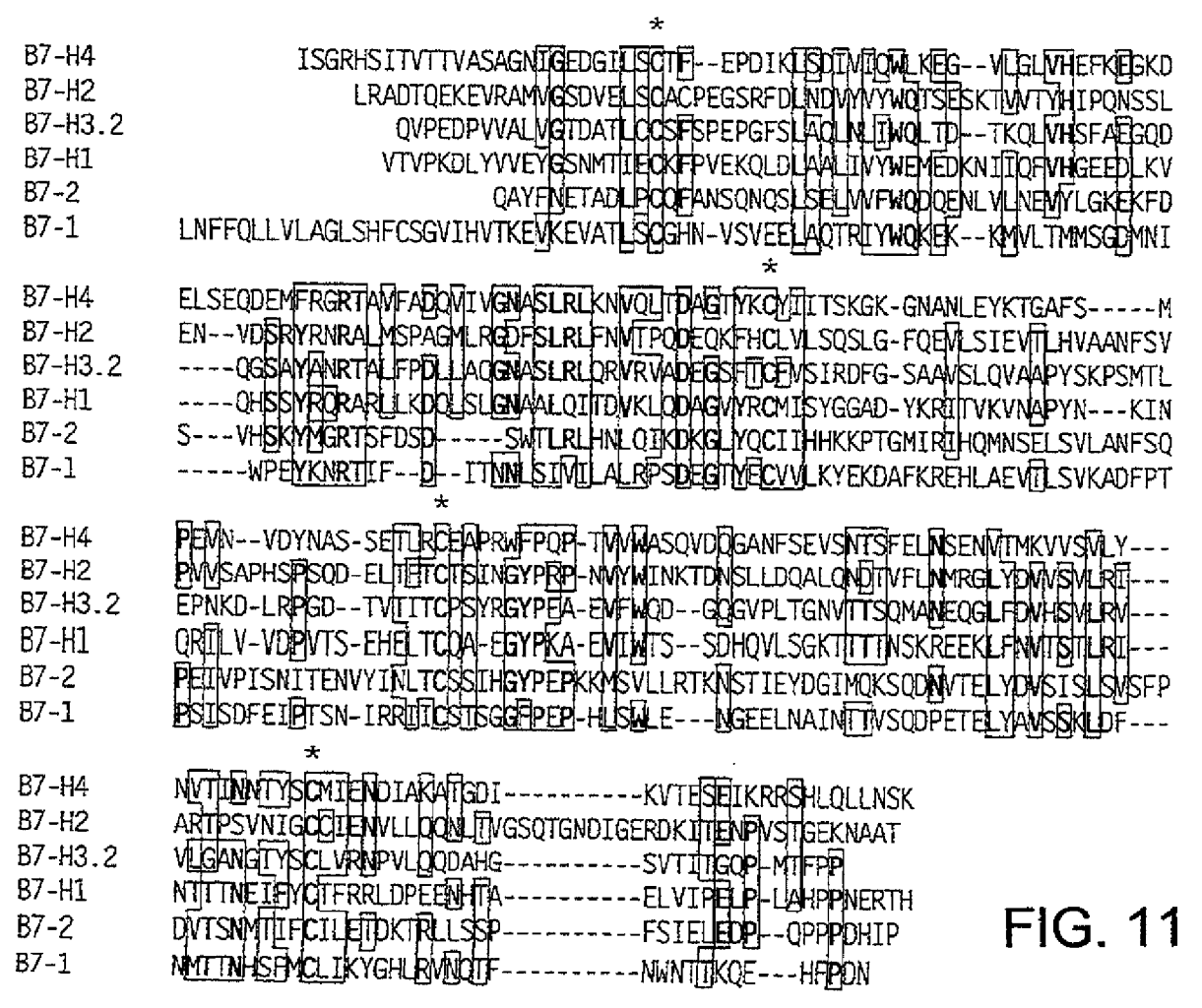

Using a strategy similar to that described above for B7-H3, the cDNA nucleotide sequence of an orf (SEQ ID NO:6) (FIG. 9) encoding another B7-homologue, B7-H4, was identified. This orf encodes a 282 amino acid protein (B7-H4; SEQ ID NO:5) (FIG. 10) which has significant homology in its predicted extracellular domain with human B7-H1, human B7-H2, human B7-H3, human B7-1, and human B7-2 (FIG. 11). The B7-H4 protein contains a typical signal peptide in its N-terminus, extracellular V- and C-like Ig domains, a transmembrane region, and a cytoplasmic tail, thereby indicating that B7-H4 is a type I transmembrane protein belonging to the Ig superfamily. Similar to the other members of the B7 family, B7-H4 has four conserved cysteine residues (marked *) that are believed to be involved in the formation of V- and C-like Ig domains. The above data suggest that B7-H4 is a member of the B7 co-stimulatory ligand family.

Northern blot analysis was performed to determine mRNA expression of the B7-H4 gene. The analysis indicated that B7-H4 mRNA is expressed at relatively high levels in the lymphoid tissues spleen and thymus and weakly in lung.

EXAMPLE 6

B7-H4Co-stimulates T Cell Proliferation

Figure 12:
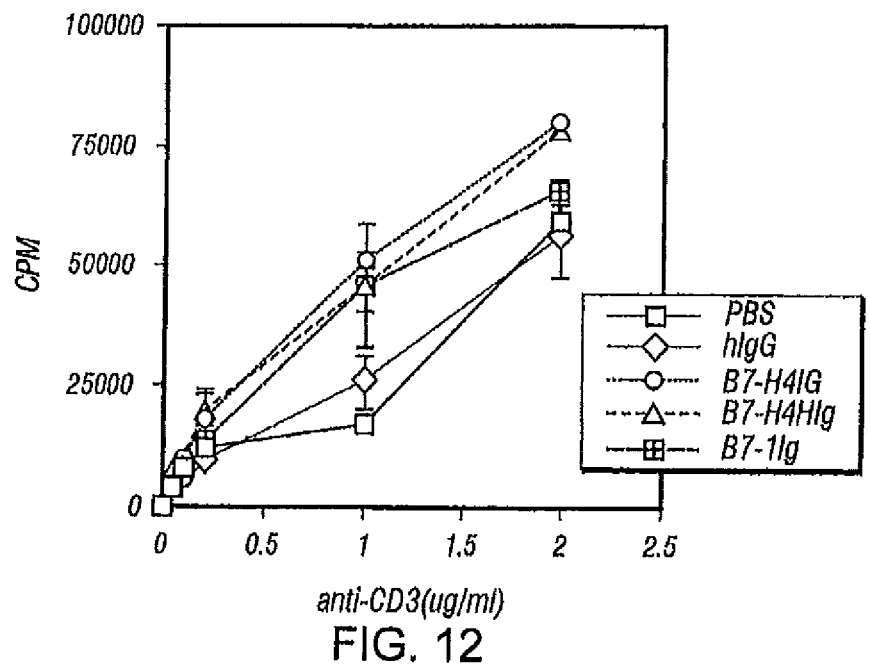
FIG. 12 is a line graph showing the proliferative response ("CPM") of nylon wool-purified T cells activated by anti-CD3 mAb (coated onto tissue culture well bottoms using the indicated concentrations) and co-stimulated by either control human IgG ("hIgG"), B7-1Ig fusion protein, B7-H4Ig fusion protein, or B7-H4hIg coated onto tissue culture well bottoms at a concentration of 5 µg/ml.
Figure 13:
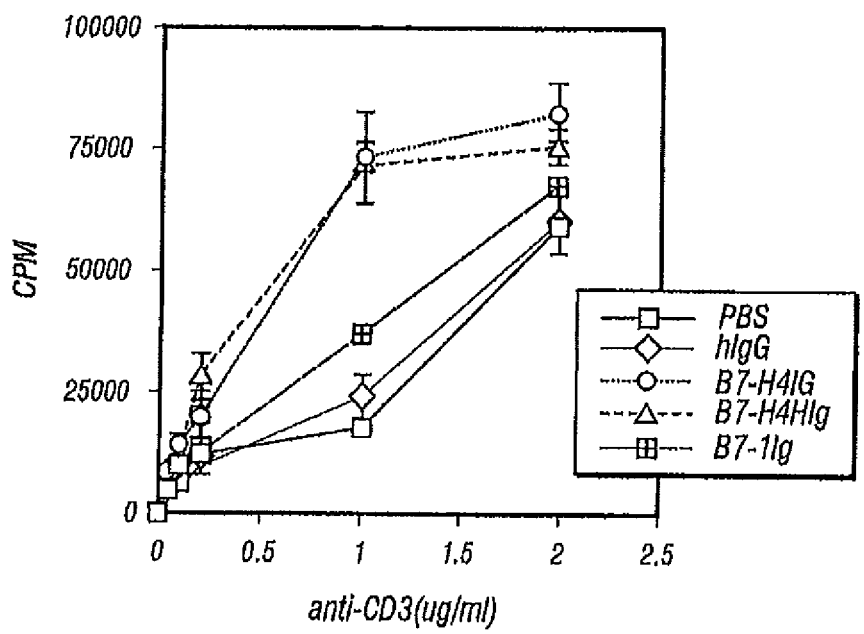
FIG. 13 is a line graph showing the proliferative response ("CPM") of nylon wool-purified T cells activated by anti-CD3 mAb (coated onto tissue culture well bottoms using the indicated concentrations) and co-stimulated by either control human IgG ("hIgG"), B7-1Ig fusion protein, B7-H4Ig fusion protein, or B7-H4hIg fusion protein coated onto tissue culture well bottoms at a concentration of 10 µg/ml.

In order to carry out T cell co-stimulation experiments, fusion proteins containing the extracellular domain of B7-H4 and the CH2-CH3 portion of either mouse IgG2a heavy chain (B7-H4Ig) or human IgG1 (B7-H4hIg) were prepared by recombinant methods substantially the same as that described above for the production of B7-H3Ig. In the co-stimulation assays, nylon wool purified T cells were stimulated in vitro by immobilized anti-CD3 mAb in the presence of the immobilized fusion proteins containing the extracellular domains of the B7-H4 (B7-H4Ig or B7-H4hIg) or B7-1 (B7-1Ig). Control culture wells contained immobilized anti-CD3 mAb and control human IgG (hIgG) or contained immobilized anti-CD3 mAb and were "mock" coated with phosphate buffered saline (PBS) ("PBS"). The anti-CD3 mAb was coated onto the bottoms of microtiter plate tissue culture wells at the indicated concentrations (FIG. 12 and FIG. 13) and the fusion or control proteins were coated onto the bottoms of the wells at either 5 µg/ml (FIG. 12) or 10 µg/ml (FIG. 13). The assays were carried out as described above for the experiments testing for B7-H3 co-stimulatory activity with T cell proliferation being expressed in terms of the amount ("CPM") of [$^3$H]-thymidine incorporated into the T cells after a 72 h culture. While coating at a concentration of 5 µg/ml resulted in a similar level of T cell co-stimulation with B7-H4Ig, B7-H4hIg, and B7-1Ig (FIG. 12), coating at a concentration of 10 µg/ml resulted in significantly higher T cell co-stimulation with B7-H4Ig and B7-H4hIg than with B7-1Ig (FIG. 13). These data indicate that B7-H4 co-stimulates the proliferation of T cells.

EXAMPLE 7

B7-H3Co-stimulates the Production Selectively of IFN-γ

Figure 14:
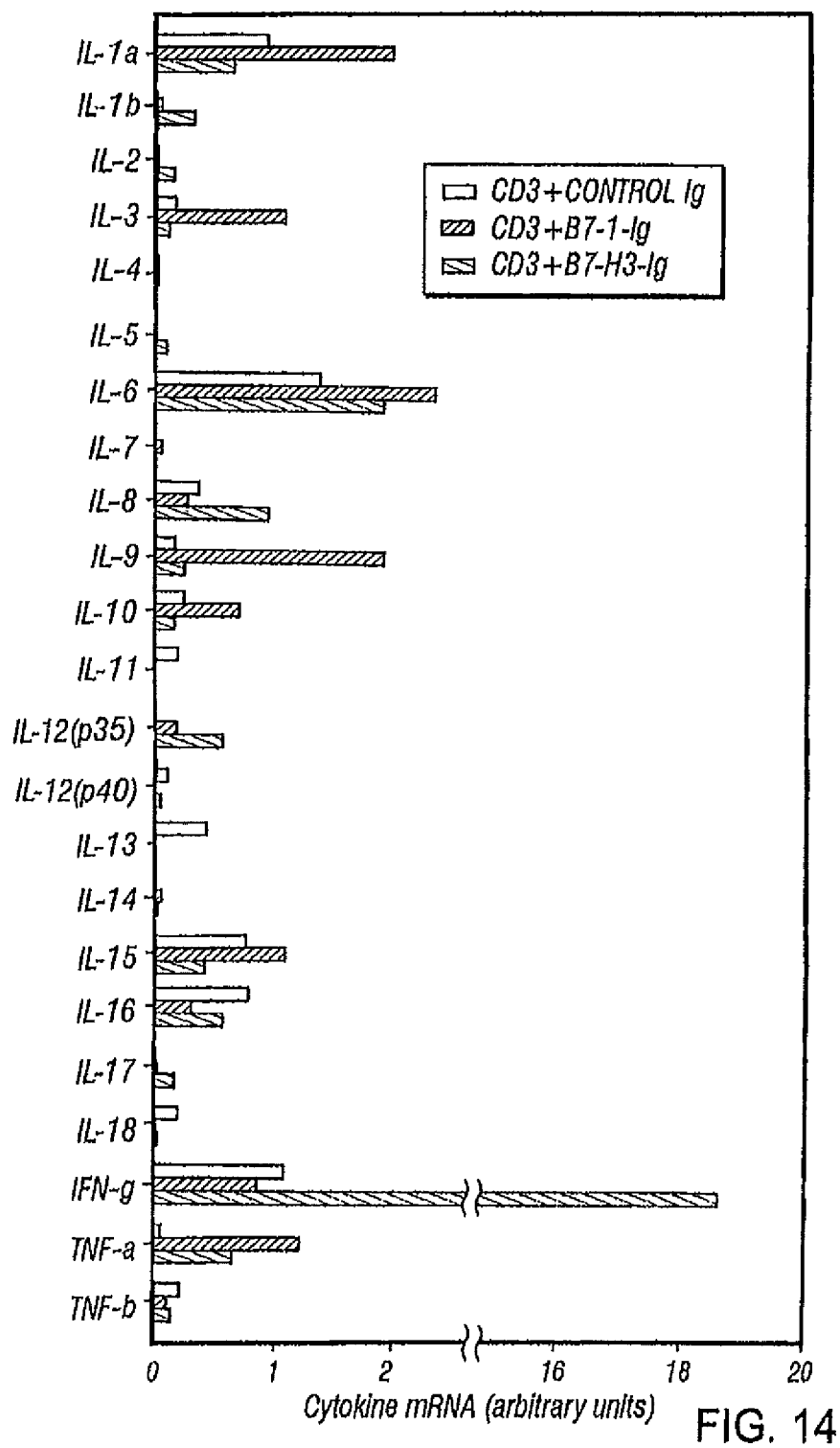
FIG. 14 is a bar graph showing the relative levels of mRNA encoding 23 cytokines in nylon wool purified T cells activated by anti-CD3 mAb (coated onto tissue culture well bottoms at a concentration of 500 ng/ml) and co-stimulated by either control human IgG (coated onto tissue culture well bottoms at a concentration of 5 µg/ml) ("hIgG"), B7-1Ig fusion protein (coated onto tissue culture well bottoms at a concentration of 5 ng/ml), or B7-H3Ig fusion protein (coated onto tissue culture well bottoms at a concentration of 5 µg/ml).

Two different assays were used to test whether B7-H3 co-stimulates the production of a variety of cytokines. The first assay employed a cytokine mRNA array to measure the relative quantities of mRNA encoding 23 different cytokines in cells activated with anti-CD3 antibody in the presence of either control Ig, B7-1Ig, or B7-H3Ig (see above). The data are shown in FIG. 14. While the presence of B7-H3Ig resulted in detectable increases in mRNA encoding several cytokines (e.g., IL-1b, IL-2, IL-5, IL-6, IL-8, IL-12 (p35), IL-17, and TNF-α), it caused a remarkable increase in the level of IFN-γ mRNA.

A previously described co-stimulation assay was used [Dong et al. (1999) *Nat. Med.* 5, 1365-1369] to test whether B7-H3 co-stimulates the production of IFN-γ, IL-2 and IL-10 at the protein level. In this assay, purified T cells were stimulated in vitro by immobilized anti-CD3 mAb in the presence of immobilized control Ig, B7-1Ig, or B7-H3Ig. After 72 h of culture, supernatants from all the cultures were removed and assayed for levels of the three cytokines by ELISA. Data obtained with T cells from four healthy human subjects are presented in Table 1; data from each individual and means±standard deviation are shown. While the presence of B7-H3Ig resulted in small but consistent increases in the level of IL-10, it resulted in dramatic increases in the level of IFN-γ.

Thus it appears that B7-H3 selectively co-stimulates the production of IFN-γ by T cells.

TABLE 1

Co-stimulation of cytokine production by B7-1Ig and B7-H3Ig

| Co-stimulatory Polypeptide | Subject | IL-2 (U/ml) | IL-10 (ng/ml) | IFN-γ (ng/ml) |
|---|---|---|---|---|
| Control Ig | 1 | 0.86 | 0.14 | 24.0 |
|  | 2 | 0.87 | 0.13 | 37.75 |
|  | 3 | 0.51 | 0.12 | 1.31 |
|  | 4 | 0.39 | 0.07 | 7.72 |
|  | Mean ± SD | 0.66 ± 12 | 0.12 ± 0.02 | 17.70 ± 8.22 |
| B7-1Ig | 1 | 0.81 | 1.29 | 23.20 |
|  | 2 | 0.72 | 1.63 | 142.40 |
|  | 3 | 1.38 | 1.03 | 8.25 |
|  | 4 | 1.67 | 0.44 | 8.50 |
|  | Mean ± SD | 1.15 ± 0.23 | 1.10 ± 0.25 | 0.87 ± 0.28 |
| B7-H3Ig | 1 | 0.53 | 0.64 | 26.61 |
|  | 2 | 0.52 | 1.66 | 247.08 |
|  | 3 | 0.89 | 0.84 | 12.58 |
|  | 4 | 0.84 | 0.34 | 10.25 |
|  | Mean ± SD | 0.69 ± 0.10 | 0.87 ± 0.28 | 74.13 ± 57.76 |

Although the invention has been described with reference to the presently preferred embodiment, it should be understood that various modifications can be made without departing from the spirit of the invention. Accordingly, the invention is limited only by the following claims.

---

The invention claimed is:

1. An isolated polypeptide consisting of an amino acid sequence encoded by a nucleic acid sequence that encodes a protein consisting of a functional extracellular region comprising at least a part of a C-like Ig domain, wherein the nucleic acid sequence hybridizes over its full length, after a wash at 50° C. to 65° C. in a buffer containing 0.2×SSC and 0.1% SDS, to the complement of the nucleotide sequence set forth in SEQ ID NO:6.

2. The isolated polypeptide of claim 1, wherein the extracellular region comprises at least a part of the C-like Ig domain of SEQ ID NO:5.

3. The isolated polypeptide of claim 1, wherein the extracellular region comprises an amino acid sequence extending from the cysteine at position 168 of SEQ ID NO:5 to the cysteine at position 225 of SEQ ID NO:5.

4. The isolated polypeptide of claim 1, wherein the polypeptide induces a suppressive response in a T cell.

5. A fusion protein comprising a first domain joined to one or more additional domains, wherein the first domain consists of a functional extracellular region comprising at least a part of a C-like Ig domain of SEQ ID NO:5 and the one or more additional domains comprises an amino acid sequence that is unrelated to SEQ ID NO:5.

6. The fusion protein of claim 5, wherein the one or more additional domains comprises an immunoglobulin constant region.

7. The fusion protein of claim 5, wherein the immunoglobulin constant region comprises CH2-CH3 regions of human IgG1.

8. The fusion protein of claim 5, wherein the fusion protein induces a suppressive response in a T cell.

9. The fusion protein of claim 5, wherein the extracellular region comprises an amino acid sequence extending from the cysteine at position 168 of SEQ ID NO:5 to the cysteine at position 225 of SEQ ID NO:5.

10. A fusion protein comprising a first domain joined to one or more additional domains, wherein the first domain consists of (a) a functional extracellular region comprising at least a part of a C-like Ig domain of SEQ ID NO:5; and (b) a fragment of the transmembrane domain of SEQ ID NO:5; and wherein the one or more additional domains comprises an amino acid sequence that is unrelated to SEQ ID NO:5.

11. The fusion protein of claim 10, wherein the first domain consists of (a) an extracellular region of B7-H4 comprising at least a part of a C-like Ig domain of SEQ ID NO:5; and (b) the transmembrane domain of SEQ ID NO:5.

* * * * *